US012209243B2

United States Patent
Miodek et al.

(10) Patent No.: US 12,209,243 B2
(45) Date of Patent: Jan. 28, 2025

(54) APTAMER-BASED CAR T-CELL SWITCH

(71) Applicant: Alaya.bio Inc., Cambridge, MA (US)

(72) Inventors: Anna Miodek, Orsay (FR); Frédéric Mourlane, Nice (FR); Cécile Bauche, Paris (FR); Renaud Vaillant, Gentilly (FR); Philippe Bishop, Las Vegas, NV (US)

(73) Assignee: Alaya.bio Inc., Cambridge, MA (US)

( * ) Notice: Subject to any disclaimer, the term of this patent is extended or adjusted under 35 U.S.C. 154(b) by 15 days.

(21) Appl. No.: 17/262,532

(22) PCT Filed: Jul. 26, 2019

(86) PCT No.: PCT/IB2019/000890
§ 371 (c)(1),
(2) Date: Jan. 22, 2021

(87) PCT Pub. No.: WO2020/021338
PCT Pub. Date: Jan. 30, 2020

(65) Prior Publication Data
US 2021/0292760 A1    Sep. 23, 2021

Related U.S. Application Data

(60) Provisional application No. 62/879,401, filed on Jul. 26, 2019, provisional application No. 62/703,869, filed on Jul. 26, 2018.

(51) Int. Cl.
| | |
|---|---|
| *C12N 15/115* | (2010.01) |
| *A61K 39/00* | (2006.01) |
| *C07K 14/47* | (2006.01) |
| *C07K 14/725* | (2006.01) |
| *C12N 5/0783* | (2010.01) |

(52) U.S. Cl.
CPC ........ *C12N 15/115* (2013.01); *A61K 39/4611* (2023.05); *A61K 39/4631* (2023.05); *A61K 39/464406* (2023.05); *A61K 39/464412* (2023.05); *A61K 39/464413* (2023.05); *A61K 39/464424* (2023.05); *A61K 39/464495* (2023.05); *C07K 14/4748* (2013.01); *C07K 14/7051* (2013.01); *C12N 5/0636* (2013.01); *C07K 2319/03* (2013.01); *C12N 2310/16* (2013.01); *C12N 2310/318* (2013.01); *C12N 2310/3519* (2013.01); *C12N 2310/51* (2013.01); *C12N 2320/13* (2013.01)

(58) Field of Classification Search
None
See application file for complete search history.

(56) References Cited

FOREIGN PATENT DOCUMENTS

| | | |
|---|---|---|
| WO | 2010144295 A1 | 12/2010 |
| WO | 2012076190 A1 | 6/2012 |
| WO | 2016127216 A1 | 8/2016 |
| WO | 2017143150 A1 | 8/2017 |
| WO | 2018128485 A1 | 7/2018 |

OTHER PUBLICATIONS

Arcangeli et al., "Switchable chimeric antigen receptor T cells: a novel universal chimeric antigen receptor platform for a safe control of T-cell activation", Translational Cancer Research, 2016, 5(S2) S174-S177.
Labrijin et al., "Bispecific antibodies: a mechanistic review of the pipeline", Nat Rev Drug Discov. 2019, 24 pages.
Liu et al., "Targeted cell-cell interactions by DNA nanoscaffold-templated multivalent bispecific aptamers", Small 2011, 7, No. 12, 1673-1682.
Pastor et al., "Targeting 4-1BB Costimulation to Disseminated Tumor Lesions With Bi-specific Oligonucleotide Aptamers", Molecular Therapy, 2011, vol. 19, No. 10, 1878-1886.
Rodgers et al., "Switch-mediated activation and retargeting of CAR-T cells for B-cell malignancies", PNAS 2016, E459-E468.
Shaffer et al., "T cells redirected against DC70 for the immunotherapy of CD70-positive malignancies", Blood, Apr. 21, 2011, vol. 117, No. 16, pp. 4304-4314.
Soldevilla et al., "MRP1-CD28 bi-specific oligonucleotide aptamers: target costimulation to drug-resistant melanoma cancer stem cells",Oncotarget. 2016, vol. 7, No. 17, pp. 23182-23196.

*Primary Examiner* — Sean McGarry
(74) *Attorney, Agent, or Firm* — Verrill Dana, LLP

(57) ABSTRACT

An aptamer-based switch technology is provided that enhances control of the use of chimeric antigen receptor (CAR)-related immunotherapies. The aptamer-based switch utilizes a synthetic bridge molecule containing a target-binding aptamer bound through a linker to a CAR-binding aptamer. A system containing a CAR and a corresponding aptameric bridge provides an immunotherapy platform that: (i) can be targeted to any desired antigen by choosing the target-binding aptamer of the bridge. (ii) can be redirected from one target to another by changing the target-binding aptamer: (iii) can be dosed according to the changing needs of an individual patient overtime by altering the administration protocol for the bridge: (iv) can be switched on or off quickly or gradually: (v) can be used as a companion diagnostic for a specific CAR therapy: (vi) can be integrated with either in vivo or ex vivo CAR expression: (vii) is non-immunogenic; and (viii) has low production costs.

26 Claims, 16 Drawing Sheets
Specification includes a Sequence Listing.

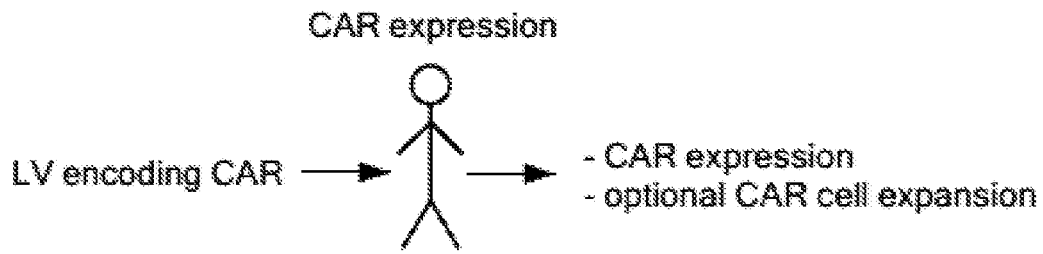
*Fig. 2A*
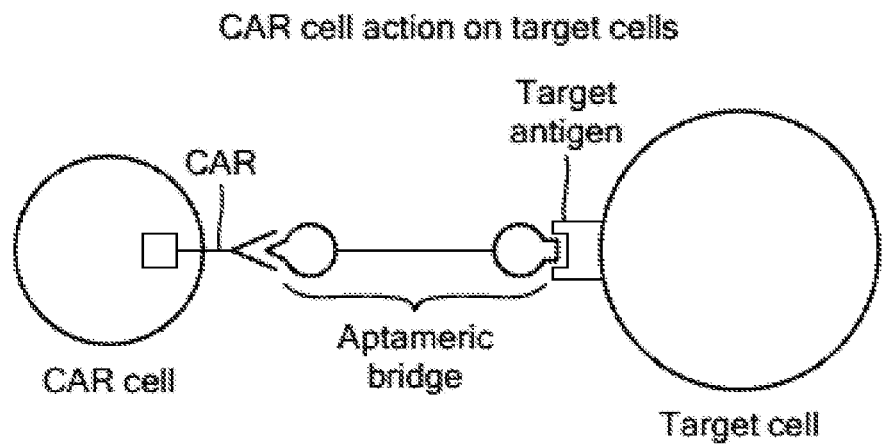
*Fig. 2B*
Modulation of immune response
- add/withdraw bridge
- change dosing regimen
- further round(s) of CAR expression
- use companion diagnostic aptamer to adjust dosing of bridge
*Fig. 2C*

| | | |
|---|---|---|
| SEQ ID NO:1 | GCN4 | NYHLENEVARLKKL |
| SEQ ID NO:2 | 15-mer SEB | ESQPDPKPDELHKSS |
| SEQ ID NO:3 | HBV pre-S2 | PRVRGLYFPAGG |
| SEQ ID NO:4 | BHV1 gpD | MEESKGYEPP |
| SEQ ID NO:5 | OmpD | DRTNNQVKA |
| SEQ ID NO:6 | GLV3 | AQEPPRQ |
| SEQ ID NO:7 | SARS-CoV | PTDSTDNNQNGGRNGARPKQRRPQ |
| SEQ ID NO:8 | A10 | GGGAGGACGAUGCGGAUCAGCCAUGUUUACGUCACUCCU |
| SEQ ID NO:9 | CELTIC_1s | TTTCCGGGTGGGGGTTTGGCACCGGGCCTGGCGCAGGGATTCG |
| SEQ ID NO:10 | CELTIC_19s | TACCGCGGGGATTGGCTCCGGGCCTGGCGTCGTAATCTGA |
| SEQ ID NO:11 | CELTIC_core | GGGTTTGGCATCGGGCCTGGC |

SEQ ID NO:12   ARACD3-3700006
UAUAGACUUUAAUGUCUCAUUUUCGCAGCGAUUCUUGUUUAUUUAACAUA 50

SEQ ID NO:13   ARACD3-
0010209UCUAAGCAAUAUUGUUUGCUUUUGCAGCGAUUCUGUUUCGAUAUAUUA

Sequences of peptide neo antigens and monomeric aptamers

Fig. 4

| A10 | CD3_CELTIC_1s | CD3_CELTIC_19s |
|---|---|---|
| | | |
| ΔG= -12.3 kcal/mol | ΔG= -5.0 kcal/mol | ΔG= -3.13 kcal/mol |

| CD3_CELTIC_core | ARACD3-3700006 | ARACD3-0010209 |
|---|---|---|
| | | |
| ΔG= -2.81 kcal/mol | ΔG= -3.80 kcal/mol | ΔG= -10.70 kcal/mol |

Predicted secondary structure of monomeric aptamers

Fig. 5

Click chemistry for linking aptamers

Binding of A10 anti-PSMA RNA aptamer on PSMA positive and negative cells (Fig. 7A) and binding of the anti-CD3 aptamers on CD3 positive and negative cells (Fig. 7B)

Visualization on an agarose gel of the anti-CAR-PNE, anti-PSMA and anti-CD3 monomers and anti-PSMAxanti-CAR-PNE and anti-PSMAxanti-CD3 aptameric dimers. RNA/RNA bispecific aptamers.

Visualization on an agarose gel of the RNA anti-PSMA and DNA anti-CD3 monomers and RNA-DNA anti-PSMAxanti-CD3 aptameric dimers. DNA/RNA bispecific aptamers.

A10 RNA aptamer stability in serum.

A10 PSMA binding properties are not altered by dimerization: Binding on PSMA positive cells is maintained after the dimerization either with RNA aptamers (anti-CD3 and anti-CAR PNE, Fig. 10A) or with DNA aptamers (anti-CD3 DNA aptamers, Fig. 10B)

Anti-CD3 RNA (Figure 11A) and DNA (Figure 11B) aptamers binding properties are not altered by dimerization: Binding on CD3 positive cells is maintained after the dimerization with anti-PSMA RNA based aptamer

```
                          1                                                        56
ARAA-00100001   (1)  UAGACCUGCAUUUCUGCAGCGAUUCUUGUUUUGCAAAAAUGCAGCUUCUAA-----
ARAA-01300011   (1)  UAGACCUGCAUUUCUGCAGCGAUUCU--UUUUGCAAAAAUG-AGCUUCUAA-----
ARAA-01700001   (1)  UAGACC---AUUUCUGCAGCGAUUCUUGUUUUGCAAAAAUGCAGCUUCUAA-----
ARAA-00600095   (1)  UAGACCUGCAUUUCUGCAGCGAUUCUUGUUUUG-AAAA--GCAG-UUCUAA-----
ARAA-05200001   (1)  UAGACCG--CUUUCUGCAGCGAUUCUUGUUUUGCAAAA-UGCAGCUUCUAA-----
                     * * * * * *      * * * * * * * * * * * * * * *   * * * * *  * * * *    *   * *   * * * * * *
```

Alignment of anti-CAR-PNE RNA aptamers

Fig. 13A

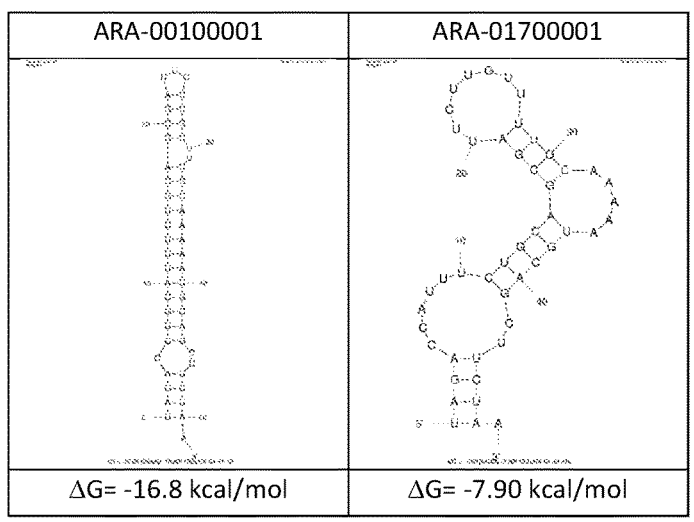

Predicted secondary structure of two anti CAR-PNE RNA aptamers

Fig. 13B

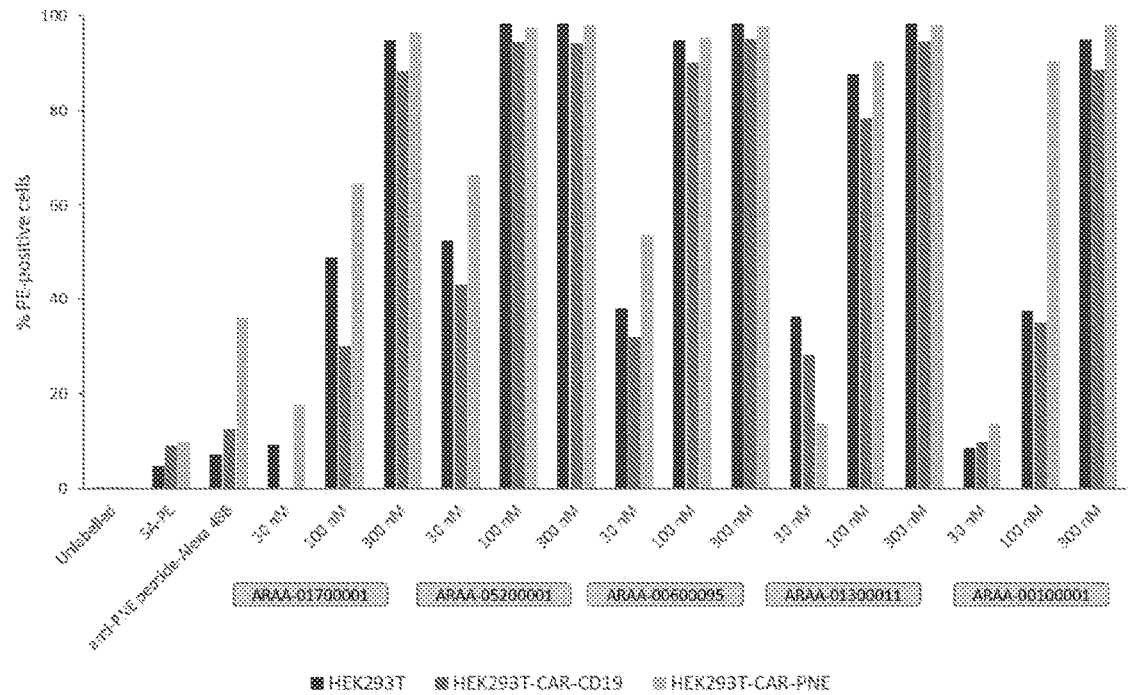
Fig. 14A
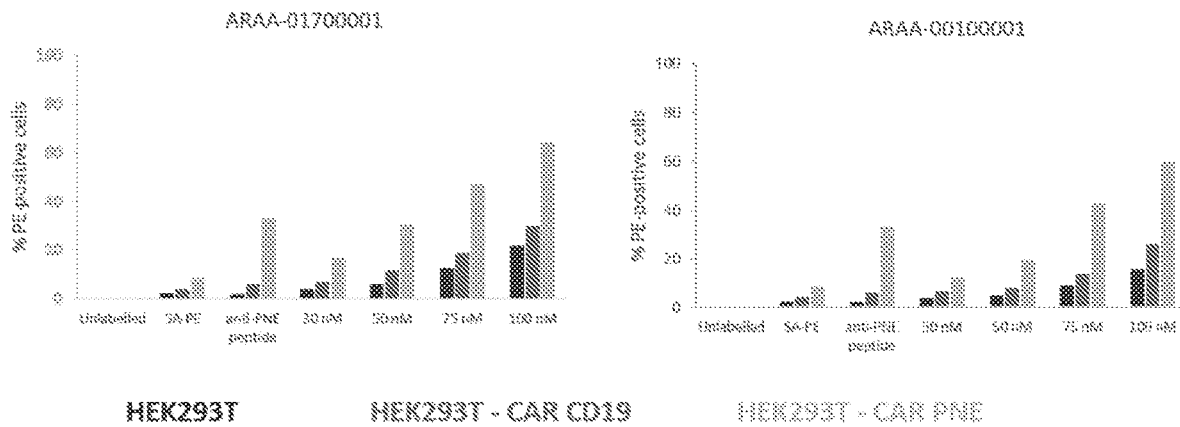
Fig. 14B
Fig. 14C
Binding of the anti-CAR PNE RNA aptamer on cells expressing no receptor, a CD19 CAR and a PNE CAR.

Stability of anti-CAR PNE RNA aptamers in presence of various concentration of serum Binding of anti-CAR PNE RNA aptamers on PBMC transduced with a CAR-PNE

SEQUENCE LISTING

```
<160> NUMBER OF SEQ ID NOS: 24

<210> SEQ ID NO 1
<211> LENGTH: 14
<212> TYPE: PRT
<213> ORGANISM: Saccharomyces cerevisiae

<400> SEQUENCE: 1

Asn Tyr His Leu Glu Asn Glu Val Ala Arg Leu Lys Lys Leu
1               5                   10

<210> SEQ ID NO 2
<211> LENGTH: 15
<212> TYPE: PRT
<213> ORGANISM: Staphylococcus aureus

<400> SEQUENCE: 2
```

```
Glu Ser Gln Pro Asp Pro Lys Pro Asp Glu Leu His Lys Ser Ser
1               5                   10                  15

<210> SEQ ID NO 3
<211> LENGTH: 12
<212> TYPE: PRT
<213> ORGANISM: Hepatitis B virus

<400> SEQUENCE: 3

Pro Arg Val Arg Gly Leu Tyr Phe Pro Ala Gly Gly
1               5                   10

<210> SEQ ID NO 4
<211> LENGTH: 10
<212> TYPE: PRT
<213> ORGANISM: Bovine herpesvirus 1

<400> SEQUENCE: 4

Met Glu Glu Ser Lys Gly Tyr Glu Pro Pro
1               5                   10

<210> SEQ ID NO 5
<211> LENGTH: 9
<212> TYPE: PRT
<213> ORGANISM: Bovine herpesvirus 1

<400> SEQUENCE: 5

Asp Arg Thr Asn Asn Gln Val Lys Ala
1               5

<210> SEQ ID NO 6
<211> LENGTH: 7
<212> TYPE: PRT
<213> ORGANISM: grapevine leafroll-associated virus 3

<400> SEQUENCE: 6

Ala Gln Glu Pro Pro Arg Gln
1               5

<210> SEQ ID NO 7
<211> LENGTH: 24
<212> TYPE: PRT
<213> ORGANISM: SARS-CoV

<400> SEQUENCE: 7

Pro Thr Asp Ser Thr Asp Asn Asn Gln Asn Gly Gly Arg Asn Gly Ala
1               5                   10                  15

Arg Pro Lys Gln Arg Arg Pro Gln
            20

<210> SEQ ID NO 8
<211> LENGTH: 39
<212> TYPE: RNA
<213> ORGANISM: Artificial Sequence
<220> FEATURE:
<223> OTHER INFORMATION: aptamer A10

<400> SEQUENCE: 8
gggaggacga ugcggaucag ccauguuuac gucacuccu                          39

<210> SEQ ID NO 9
<211> LENGTH: 43
<212> TYPE: DNA
<213> ORGANISM: artificial sequence
<220> FEATURE:
```

```
<223> OTHER INFORMATION: aptamer CELTIC_1s

<400> SEQUENCE: 9
tttccgggtg ggggtttggc accgggcctg gcgcagggat tcg          43

<210> SEQ ID NO 10
<211> LENGTH: 40
<212> TYPE: DNA
<213> ORGANISM: artificial sequence
<220> FEATURE:
<223> OTHER INFORMATION: aptamer CELTIC_19s

<400> SEQUENCE: 10
taccgcgggg attggctccg ggcctggcgt cgtaatctga              40

<210> SEQ ID NO 11
<211> LENGTH: 21
<212> TYPE: DNA
<213> ORGANISM: artificial sequence
<220> FEATURE:
<223> OTHER INFORMATION: aptamer CELTIC_core

<400> SEQUENCE: 11
gggtttggca tcgggcctgg c                                  21

<210> SEQ ID NO 12
<211> LENGTH: 50
<212> TYPE: RNA
<213> ORGANISM: artificial sequence
<220> FEATURE:
<223> OTHER INFORMATION: aptamer ARACD3 3700006

<400> SEQUENCE: 12
uauagacuuu aaugucucau uuucgcagcg auucuuguuu auuuaacaua   50

<210> SEQ ID NO 13
<211> LENGTH: 48
<212> TYPE: RNA
<213> ORGANISM: artificial sequence
<220> FEATURE:
<223> OTHER INFORMATION: aptamer ARACD3-0010209

<400> SEQUENCE: 13
ucuaagcaau auuguuugcu uuugcagcga uucuguuucg auauauua     48

<210> SEQ ID NO 14
<211> LENGTH: 97
<212> TYPE: DNA
<213> ORGANISM: Artificial Sequence
<220> FEATURE:
<223> OTHER INFORMATION: template for aptamer production
<220> FEATURE:
<221> NAME/KEY: misc_feature
<222> LOCATION: (24)..(43)
<223> OTHER INFORMATION: n is a, c, g, or t
<220> FEATURE:
<221> NAME/KEY: misc_feature
<222> LOCATION: (65)..(74)
<223> OTHER INFORMATION: n is a, c, g, or t

<400> SEQUENCE: 14
cctctctatg ggcagtcggt gatnnnnnnn nnnnnnnnnn nntttctgc agcgattctt   60 gtttnnnnnn nnnnggagaa tgaggaaccc agtgcag                          97

<210> SEQ ID NO 15
<211> LENGTH: 43
```

```
<212> TYPE: DNA
<213> ORGANISM: Artificial Sequence
<220> FEATURE:
<223> OTHER INFORMATION: primer

<400> SEQUENCE: 15
taatacgact cactataggg cctctctatg ggcagtcggt gat            43

<210> SEQ ID NO 16
<211> LENGTH: 23
<212> TYPE: DNA
<213> ORGANISM: Artificial Sequence
<220> FEATURE:
<223> OTHER INFORMATION: primer

<400> SEQUENCE: 16
ctgcactggg ttcctcattc tcc                                  23

<210> SEQ ID NO 17
<211> LENGTH: 23
<212> TYPE: DNA
<213> ORGANISM: Artificial Sequence
<220> FEATURE:
<223> OTHER INFORMATION: Blocking sequence

<400> SEQUENCE: 17
atcaccgact gcccatagag agg                                  23

<210> SEQ ID NO 18
<211> LENGTH: 23
<212> TYPE: DNA
<213> ORGANISM: Artificial Sequence
<220> FEATURE:
<223> OTHER INFORMATION: Blocking sequence

<400> SEQUENCE: 18
ctgcactggg ttcctcattc tcc                                  23

<210> SEQ ID NO 19
<211> LENGTH: 15
<212> TYPE: DNA
<213> ORGANISM: Artificial Sequence
<220> FEATURE:
<223> OTHER INFORMATION: Capture sequence
<220> FEATURE:
<221> NAME/KEY: 5'-cap
<222> LOCATION: (1)..(1)
<223> OTHER INFORMATION: 5' end capped with biotin-gtc-PEG6spacer

<400> SEQUENCE: 19
caagaatcgc tgcag                                           15

<210> SEQ ID NO 20
<211> LENGTH: 51
<212> TYPE: RNA
<213> ORGANISM: Artificial sequence
<220> FEATURE:
<223> OTHER INFORMATION: RNA aptamer ARAA-00100001

<400> SEQUENCE: 20
uagaccugca uuucugcagc gauucuuguu uugcaaaaau gcagcuucua a   51

<210> SEQ ID NO 21
<211> LENGTH: 48
<212> TYPE: RNA
<213> ORGANISM: Artificial sequence
<220> FEATURE:
```

```
<223> OTHER INFORMATION: RNA aptamer ARAA-01300011

<400> SEQUENCE: 21
uagaccugca uuucugcagc gauucuuuuu gcaaaaauga gcuucuaa          48

<210> SEQ ID NO 22
<211> LENGTH: 48
<212> TYPE: RNA
<213> ORGANISM: Artificial sequence
<220> FEATURE:
<223> OTHER INFORMATION: RNA aptamer ARAA-01700001

<400> SEQUENCE: 22
uagaccauuu cugcagcgau ucuuguuuug caaaaaugca gcuucuaa          48

<210> SEQ ID NO 23
<211> LENGTH: 47
<212> TYPE: RNA
<213> ORGANISM: Artificial sequence
<220> FEATURE:
<223> OTHER INFORMATION: RNA aptamer ARAA-00600095

<400> SEQUENCE: 23
uagaccugca uuucugcagc gauucuuguu uugaaaagca guucuaa           47

<210> SEQ ID NO 24
<211> LENGTH: 48
<212> TYPE: RNA
<213> ORGANISM: artificial sequence
<220> FEATURE:
<223> OTHER INFORMATION: RNA aptamer ARAA-05200001

<400> SEQUENCE: 24
uagaccgcuu ucugcagcga uucuuguuuu gcaaaaugca gcuucuaa          48
```

APTAMER-BASED CAR T-CELL SWITCH

BACKGROUND

Chimeric antigen receptors (CARs) utilize single-chain variable domain (scFv) antibodies to endow a patient's T-cells with the ability to recognize and kill cancer cells. However, in spite of early successful application, the use of CAR T-cells has been complicated by difficulties in controlling immune responses in vivo, which can result in harmful excessive release of cytokines and or undesired toxicities. Further, off-target reactions can occur, and antigenic escape by tumors can create a need for subsequent rounds of CAR T-cell therapy with modified antigen specificity. Thus, there is a need to develop strategies to strengthen interactions to increase specificity, to redirect the CAR to new antigens, or to develop "off" or "kill" switches to inhibit or terminate CAR T-cell therapy.

Switchable CAR T-cell approaches have been developed that allow administration of an adaptable molecular switch to the patient which mediates interaction between a CAR T-cell and a target cell. In the absence of the switch, no CAR-mediated immune response occurs. For example, kill switches can be used to eliminate CAR-T cells and prevent toxicity (Straathof et al., Di Stasi et al.). Another approach utilizes a split chimeric receptor which associates in the presence of a small molecule switch (Wu et al.). Antibody-based switches also have been developed, which mediate the interaction between the CAR and target (Tamada, et al., Urbanska, et al. (2012a), Urbanska et al. 2012b)). In a variant of antibody switch technology, a target-specific antibody can be integrated with a peptide neo-epitope (PNE) which binds to the scFv portion of the CAR (Rodgers et al.). The PNE is different from endogenous epitopes, and enables a modular switch approach in which new switches can be engineered by combining a single PNE and anti-PNE CAR with different target-specific antibodies. However, this approach still requires the complex engineering of antibody molecules, and creates the potential for immune reactions to the switch, particularly if the scFv is not fully humanized.

SUMMARY

The present technology provides an aptamer-based switch technology that creates a high degree of control when carrying out chimeric antigen receptor (CAR)-related immunotherapies. The aptamer-based switch, or aptameric bridge, of the present technology, at its most basic level, utilizes a synthetic bridge molecule containing a target-binding aptamer bound through a linker to a CAR-binding aptamer. A system containing a CAR and a corresponding aptameric bridge provides an immunotherapy platform that: (i) can be targeted to any desired antigen by choosing the target-binding aptamer of the bridge, (ii) can be redirected from one target to another by changing the target-binding aptamer; (iii) can be dosed according to the changing needs of an individual patient over time by altering the administration protocol for the bridge; (iv) can be switched on or off quickly or gradually; (v) can be used as a companion diagnostic for a specific CAR therapy; (vi) can be integrated with either in vivo or ex vivo CAR expression; (vii) is non-immunogenic; and (viii) has low production costs.

The present technology provides cell redirecting aptamers (e.g., bispecific or multivalent aptamers), which can be used as aptameric bridges in aptamer-based CAR immunotherapy systems as well as for in vivo or ex vivo genetic modification of cells. The aptameric bridges, cells, kits, and methods of the present technology can be employed in a wide variety of uses, including as immunotherapies for the treatment of cancers (e.g., hematologic or non-hematologic, individual cells or solid tumors), autoimmune diseases (e.g. arthritis, myasthenia gravis, pemphigus), neuroinflammatory diseases, ophthalmic diseases, neurodegenerative diseases (e.g., ALS, Huntington's disease, Alzheimer's disease), neuromuscular diseases (including Duchenne muscular dystrophy, SMA), infectious diseases (e.g., HIV, HSV, HPV, HBV, Ebola, tuberculosis, *Cryptococcus*), and metabolic diseases (e.g., Type 1 diabetes mellitus). They also can be used to provide diagnostic agents, kits, and methods for use in such immunotherapies, including imaging, analysis of cell trafficking, and research and development of new immunotherapies, as well as to provide prophylaxis when combined with stem cell therapies (e.g., HSCT).

As used herein, "chimeric antigen receptor cells" or "CAR cells" are genetically modified cells (e.g., T-cells, NK-cells, monocytes, or others), that have been manipulated ex vivo or in vivo to express a single-chain variable domain (scFv) antibody fused, through a stalk or transmembrane domain, to the intracellular domain of a receptor (e.g., CD3-TCR) so as to endow the cell with the ability to recognize and bind one or more specific antigens and activate a cellular immune response (e.g., kill cancer cells or destroy a virus-infected cell).

As used herein, "antigenic loss" or "antigenic escape" can refer to any of several mechanisms of resistance or adaptation to immunotherapy, such as downregulation of a tumor antigen or upregulation of inhibitory ligands (e.g., PD-L1, TIM3, LAG3) which contributes to CAR-T cell failure, failure of a CAR cell to get to its target (e.g., a tumor site), immunity against the antibody portion of a CAR (e.g., T-cell response against the scFv, particularly if it is not fully humanized), CAR-T cell fitness (i.e., diminished potential for memory self-renewal and increased propensity for exhaustion), or antigen splicing or mutation.

Candidate aptamers are a set of nucleic acids of differing sequence, from which a desired aptamer is selected. The source of candidate aptamers can be naturally-occurring nucleic acids or fragments thereof, chemically synthesized nucleic acids, enzymatically synthesized nucleic acids, or nucleic acids made by a combination of the foregoing techniques.

A nucleic acid for use in the present technology can be, for example, a DNA, RNA, or XNA (xeno nucleic acid) molecule, including any chemical modification thereof, and can be either single-stranded, double-stranded, or a mixture of single-stranded and double-stranded.

A target is a structural unit, usually a component of a biological entity, that binds to an aptamer. The target can be a molecule, such as a protein, peptide, carbohydrate, polysaccharide, glycoprotein, hormone, receptor, antigen, antibody, virus, substrate, metabolite, drug, nutrient, growth factor, or the like. The target can be a part of a cell or a cell, such as a T cell, an NK cell, a monocyte, a B-cell, a tumor cell, or a cell that is pathologically altered (e.g., by a virus or other microorganism, or altered to due to genetic rearrangements). The target also can be an organ or an organelle.

Binding affinity refers to the strength of interactions between two or more structures, such as a ligand and a receptor, that reversibly bind to each other. Binding affinity is a measure of dynamic equilibrium of the ratio of on-rate ($k_{on}$) and off-rate ($K_{off}$), and can be measured or estimated by any known method, including determination of the dissociation constant ($K_d$) or association constant ($K_a$), such as from the concentration dependence of binding, or determination of the Gibbs free energy of dissociation ($\Delta G_d$). Increased binding affinity arises from stronger intermolecular forces between the structures interacting (e.g., ligand and receptor) and results in increased residence time at the binding site. Ligands displaying higher binding affinity can have higher "on" rates and/or lower "off" rates. Increased binding affinity can be advantageous in therapeutic products since full receptor activity is achieved with lower concentration of ligand. Binding affinity can be determined by the collective strength of multiple affinities of individual non-covalent binding interactions in a multivalent structure. The overall binding affinity of a multivalent ligand is dependent on its individual binding affinities, valency of both ligand and receptor, and steric arrangement of the structures that interact. However, the overall binding affinity of a multimeric construct is not merely the average of individual binding affinities of the individual aptamers. Factors that influence the affinity of a multimeric structure include the stereochemical fit between ligand and receptor, size of the contact area between them and distribution of charged and hydrophobic groups.

Safety profile refers to the collection of adverse effects associated with a drug, therapy or intervention, as well as with the likelihood of such adverse effects. A better safety profile can result from less frequent and/or less severe adverse reactions and/or adverse events being associated with the same level of therapeutic benefit. A better safety profile can be associated with an improved therapeutic index (TI), i.e., a larger safety window between a minimum effective dose and a maximum tolerated dose.

Immune response refers to the induction of humoral and/or cell-mediated responses specific against an antigen. The humoral component can include production of antibodies specific for an antigen, while the cell-mediated component can include the generation of delayed-type hypersensitivity and cytotoxic effector cells against an antigen. Immune cells participate in the immune response through a variety of ways, including direct interaction with an antigen, interaction with other cells of the immune system, and by releasing and/or reacting to cytokines.

Activation or stimulation of the immune system can be mediated by the activation of immune effector cells, such as lymphocytes, macrophages, dendritic cells, natural killer cells (NK cells), and cytotoxic T lymphocytes (CTL). It can be mediated by activation and maturation of antigen presenting cells, such as dendritic cells. It also can be mediated by the blockade of inhibitory pathways, such as by inhibiting immune checkpoint molecules.

BRIEF DESCRIPTION OF THE DRAWINGS

FIG. 2 shows a schematic representation of a system and method for CAR T-cell therapy using in vivo expression of a CAR platform together with targeting mediated by aptameric bridges.

FIG. 4 is a listing of sequences of peptide neoantigens and monomeric aptamers.

FIG. 5 shows some predicted secondary structures of monomeric aptamers. The depicted aptamers are A10 (SEQ ID NO:8), CELTIC_1s (SEQ ID NO:9), CELTIC_19s (SEQ ID NO:10), CELTIC_core (SEQ ID NO:11), ARACD3 3700006 (SEQ ID NO:12), and ARACD3-0010209 (SEQ ID NO:13).

FIG. 13A shows a sequence alignment of several anti-PNE RNA aptamers. The aptamers depicted are ARAA-00100001 (SEQ ID NO:20), ARAA-01300011 (SEQ ID NO: 21), ARAA-01700001 (SEQ ID NO:22), ARAA-00600095 (SEQ ID NO:23), and ARAA-05200001 (SEQ ID NO:24). FIG. 13B shows the predicted secondary structure of two of the RNA aptamers from 13A, ARAA-00100001 (SEQ ID NO:20) and ARAA-01700001 (SEQ ID NO:22).

FIGS. 14A-14C show the binding of anti-CAR PNE aptamers on cells expressing no receptor, a CD19 CAR or a PNE CAR.

DETAILED DESCRIPTION

Figure 1:
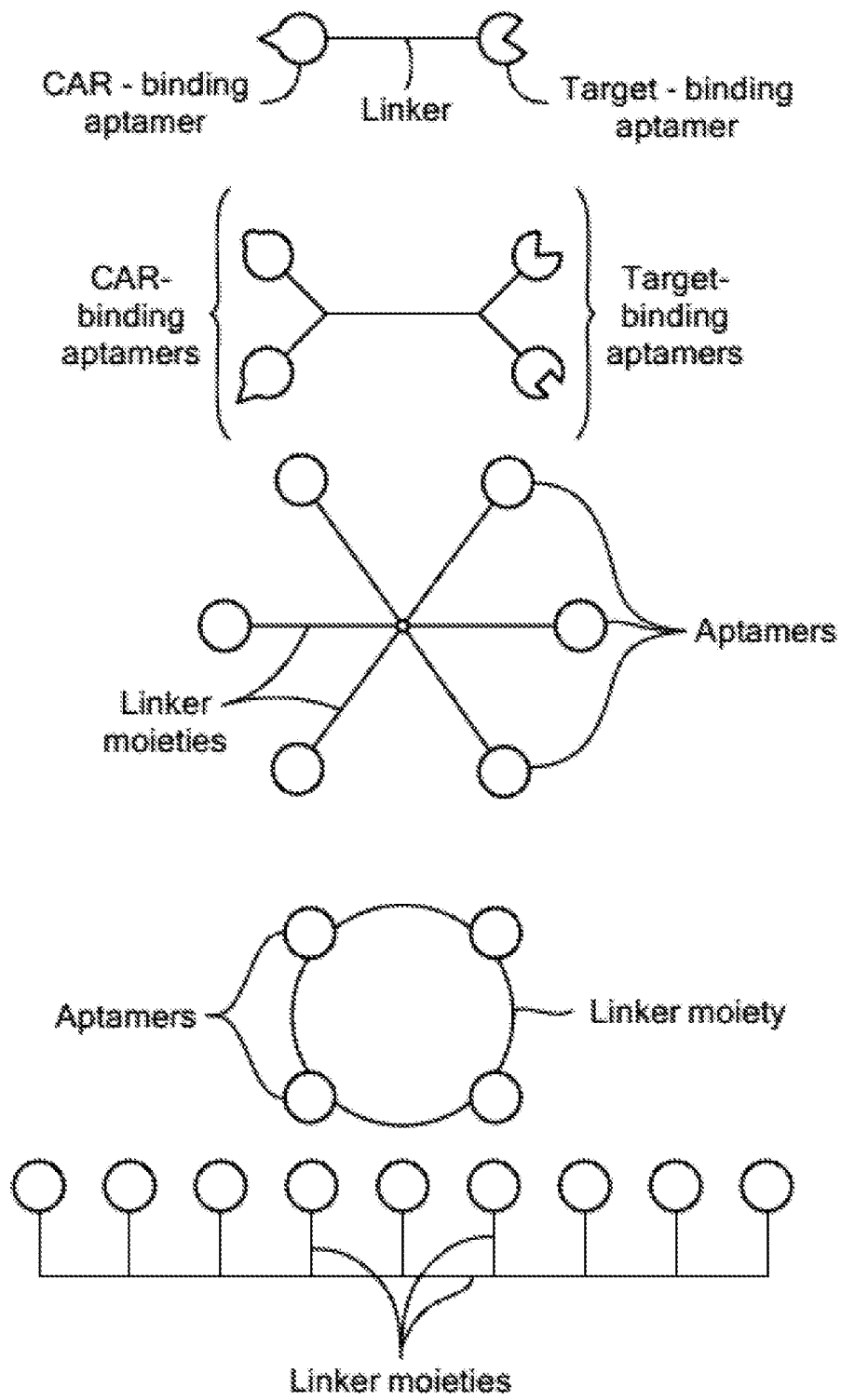
FIG. 1 shows schematic representations of several embodiments of aptameric bridges of the present technology.
Figure 3A:
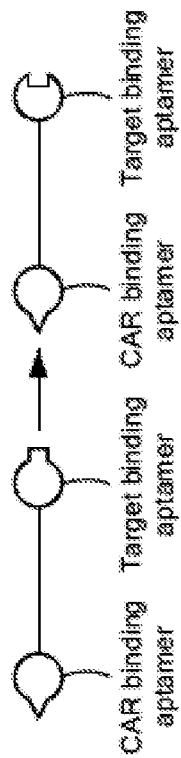
FIG. 3 is a schematic representation of methods of target redirection according to the present technology.
Figure 3B:
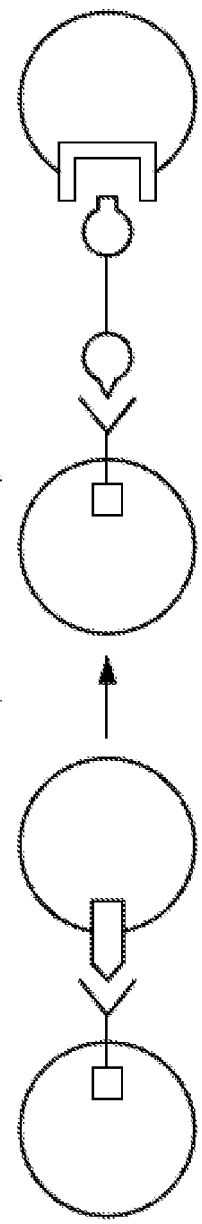
Figure 3C:
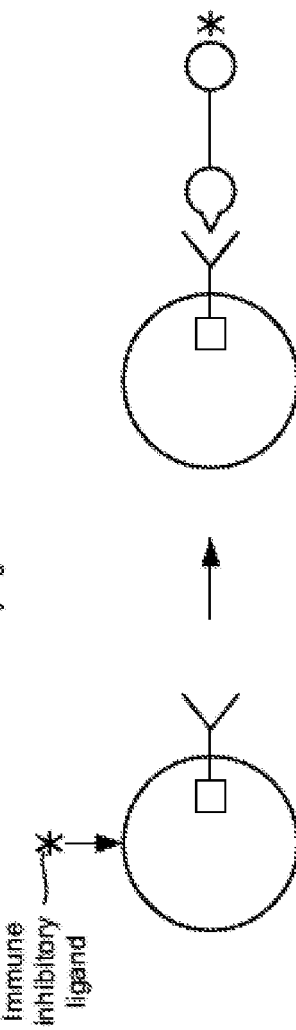
Figure 6:
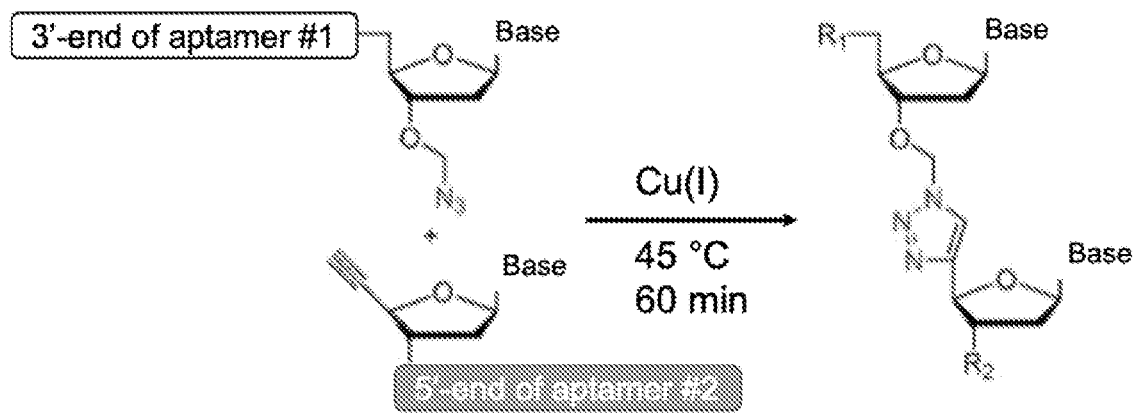
FIG. 6 shows a scheme for a click chemistry reaction to link aptamers.

The present technology provides aptamer-based switches for use in immunotherapies such as CAR T-cell therapy. Aptameric switches serve as physical bridges between CAR-expressing immune cells and target cells, such as cancer cells or cells of a pathogen. However, aptameric switches or bridges also serve as agile and quickly adaptable tools for modulating the specificity and intensity of an immune reaction. Because their CAR-binding and target-binding functions are both carried out by aptamers, aptameric bridges can be rapidly selected and adapted to the evolving needs of a patient in vitro at a rapid pace and low cost that cannot be matched by antibody-based approaches. Moreover, the aptameric bridges of the present technology can be combined with direct injection of a vector coding for a CAR, e.g., from polymer-coated viral vector particles, and the in vivo transduction (i.e., transduction within the body of the subject of the immunotherapy) of the selected immune cells and expression of CARs, to achieve advanced immunotherapy with further time and cost savings compared with conventional ex vivo transduction and expansion of CAR T-cells.

The cell redirecting aptamer technology (e.g., bispecific or multivalent binding) and aptameric bridges of the present technology, as well as systems and kits containing them, can be used in various applications, including autologous or heterologous cancer therapy and immunotherapy. The cell redirecting aptamer technology, aptameric bridges, aptamer-based CAR immunotherapy systems, kits, and methods of the present technology can be employed in a wide variety of immunotherapies, including treatment of cancers (e.g., hematologic or non-hematologic, individual cells or solid tumors), autoimmune diseases (e.g. arthritis, myasthenia gravis, pemphigus), neuroinflammatory diseases, ophthalmic diseases, neurodegenerative diseases (e.g., ALS, Huntington's disease, Alzheimer's disease), neuromuscular diseases (Duchenne disease, SMA), infectious diseases (e.g., HIV, HSV, HPV, HBV, Ebola, tuberculosis, *Cryptococcus*), and metabolic diseases (e.g., Type 1 diabetes mellitus). They also can be used to provide diagnostic agents, kits, and methods for use in such immunotherapies, including imaging, analysis of cell trafficking, and research and development of new immunotherapies, as well as to provide prophylaxis when combined with stem cell therapies (e.g., HSCT).

Aptameric bridges can enhance immunotherapy by improving the quality and intensity of an immune response, such as a cell-mediated immune response directed against cancer or infection. Further, aptameric bridges can be used to direct a universal CAR to many different targets, as well as to redirect an immune response to a different target. Aptameric bridges also can be used to tune the strength of an immune response, or to turn the response on or off, simply by administering differently targeted aptameric bridges or adjusting the dose or administration schedule of an aptameric bridge over time. A further use of aptameric bridges is to convert inhibitory ligands such as PDL-1 to immune stimulatory effects, namely by replacing the target-binding aptamer of an aptameric bridge with an aptamer binding the inhibitory ligand, thereby converting the inhibitory ligand to a CAR-binding ligand.

CAR therapy according to the present technology typically begins with introduction of CAR-expressing cells into a subject in need of immunotherapy. The CAR cells can be obtained ex vivo, for example, by transducing cells removed from the subject with a viral vector, or transfecting them with a plasmid or transposon, that causes CARs to be expressed on the cells, followed by expansion of the cells in culture medium and introduction of the expanded cells into the subject, such as by intravenous injection. Alternatively, a viral vector, such as a lentiviral vector, encoding the CAR can be administered to the subject, e.g., by intravenous injection, whereupon the CAR is expressed in desired immune cells (such as autologous or allogenic T-cells, NK-cells, B-cells, monocytes, macrophages, or dendritic cells). In either method, once a baseline of CAR-expressing cells is established within the subject's body, the CAR cells will multiply when activated by binding of a target to the scFv portion of the CAR.

Administration of an appropriate aptameric bridge to a subject containing a sufficient number of CAR cells will elicit an immune response against the target specified by the target-binding aptamer of the bridge upon binding of the CAR-binding aptamer of the bridge to the CAR. The strength of the resulting immune response, which may change over time, is a function of the number of CAR cells in the subject, access of the CAR cells to the target, and the concentration of aptameric bridge at the target. The strength of the immune response can be adjusted up or down by adjusting the number of CAR cells and/or by adjusting the concentration of the bridge by increasing or decreasing the amount of bridge administered or reducing or increasing the time interval between doses of the bridge administered.

In a therapeutic method of the present technology, the total quantity of CAR cells in the subject is estimated prior to administering the aptameric bridge to start immunotherapy, and the administration protocol (e.g., dose amount, number of doses, and/or administration interval) is designed (e.g., using an algorithm) so that a desired strength and/or duration of immune response is produced. The strength of the immune response can be monitored using known methods (e.g., using fluorescent activated cell sorting (FACS) analysis to quantify the number and type of certain activated immune cells in a blood sample from the patient, or by determining the levels of certain cytokines in such a sample. If the immune response is too strong, and could present a danger to the patient, the response can be reduced by reducing the amount or frequency of administration of the aptameric bridge, by stopping it altogether, or by administering a "kill" switch that includes either the single CAR-binding aptamer (which would disrupt binding of the aptameric bridge to the CAR), a peptide or antibody that binds to the CAR and disrupts binding of the aptameric bridge, the single target-binding aptamer (which would disrupt binding of the aptameric bridge to the target), or a soluble domain or epitope from the CAR or target antigen.

An aptameric bridge of the present technology can be used to redirect CAR cells to a different target. This can be useful in the event of antigenic escape by the first target, or a weak response against the first target, necessitating pursuit of a different or additional target. In one embodiment of the method, a different (e.g., second or later) aptameric bridge is administered to the subject, which has the same or similar CAR-binding aptamer but a different target-binding aptamer than the first bridge. In another embodiment, a conventional CAR which is targeted directly to a first target (i.e., without the use of a CAR switch) is expressed on cells in the subject, and an aptameric bridge is administered to the subject to redirect the CAR response to a different (second or higher) target; the aptameric bridge would include a CAR-binding aptamer specific for the target-binding CAR and a target-binding aptamer, with the two aptamers bound by a linker. This approach can be used several times (e.g., 2, 3, 4, 5, or more times) sequentially or simultaneously with different targets in the same subject in order to tune the immunotherapy or to find an optimum target or combination of targets. An embodiment of the aptameric bridge of the present technology is bound to a detectable label for use in imaging or quantifying either the CAR cells or targets within the subject. For example, the bridge can include an 18F moiety attached to the linker or to either a CAR-binding aptamer or a target-binding aptamer for use with PET scanning. The same method can be practiced using an individual aptamer (either CAR-binding or target-binding) which is used in the aptameric bridge for therapy. This method can be employed, for example, to quantify CAR cells in the subject before beginning therapy or during therapy.

An aptameric bridge of the present technology contains two or more aptamers covalently or non-covalently bound by a linking moiety. The two or more aptamers form a CAR-binding portion and a target-binding portion, each of which contains one or more aptamers. The CAR-binding aptamer binds to a CAR expressed in an immune cell, such as a T cell, and in some embodiments activates the immune cell but in other embodiments (e.g., when acting as a "kill" switch) does not activate the immune cell. The target is an intended target of immunotherapy, i.e., a cell intended for elimination. Thus, the CAR-expressing cell and aptameric bridge are intended for use together as a system in an immunotherapy, such as CAR-T cell therapy. Binding of the aptameric bridge to the CAR as well as to the target is preferably high affinity binding. The target can be a protein (such as a cell-surface receptor protein), a cell, a small molecule, or a nucleic acid. The target is preferably located on the surface of a target cell, such as a cancer cell, and may or may not be found on other cells (normal cells) of the subject.

In some embodiments, the target is a tumor antigen, such as CD19, CD20, CD22, CD30, CD123, BCMA, NY-ESO-1, mesothelin, PSA, PSMA, MART-1, MART-2, Gp100, tyrosinase, p53, ras, Ftt3, NKG2D Ligangs, Lewis-Y, MUC1, SAP-1, survivin, CEA, Ep-CAM, Her2, Her3, EGFRvlll, BRCA1/2, CD70, CD73, CD16A, CD40, VEGF-α, VEGF, TGF-β, CD32B, CD79B, cMet, PCSK9, IL-4RA, IL-17, IL-23, 4-1BB, LAG-3, CTLA-4, PD-L1, PD-1, OX-40, or mutated SOD. Component aptamers of an aptameric bridge also can specifically bind to combinations of such targets. In some embodiments, the target is an antigen of an infectious agent, such as gag, reverse transcriptase, tat, HIV-1 envelope protein, circumsporozoite protein, HCV nonstructural proteins, hemaglutinins; an aptamer bridge also can specifically bind to combinations of such targets.

In a preferred embodiment, the CAR-binding aptamer or aptamers are selected for specific binding to the extracellular domain of a CAR having affinity for a peptide neo-epitope (PNE), i.e., an anti-PNE CAR. Since the PNE is an epitope that does not exist within the subject's body, immune cells expressing the anti-PNE CAR are not activated by endogenous biomolecules, but await the administration to the subject of the aptameric bridge, which serves as an "on" switch for the immune cells and targets the CAR-expressing cells toward a desired antigen(s) or cell type(s) bearing the antigen(s). The immune activation and in vivo expansion of the CAR-expressing immune cells can be turned off by administration to the subject of a peptide containing the PNE or of either the CAR-binding aptamer or target-binding aptamer of the bridge in monomeric form, any one of which will terminate the activation of the CAR-expressing immune cells by the target.

The PNE can be any peptide epitope not found in the host's proteome (e.g., not found in the human proteome), for which an anti-PNE CAR can be obtained. An example of a preferred PNE is a peptide fragment of the GCN4 transcription factor from *Saccharomyces cerevisiae* (NYHLENEVARLKKL, SEQ ID NO:1). A CAR binding GCN4 with high affinity ($K_d$=5.2 pM) and including the 52SR4 single chain antibody is described by Rodgers et al. Further PNEs suitable for use with a CAR and corresponding aptameric bridge include: (i) the N-terminal 15-mer peptide ESQPDPKPDELHKSS (SEQ ID NO:2) of Staphylococcal enterotoxin B, paired with an antibody binding thereto and described in Clin. Vaccine Immunol. 17 (11): 1708-1717; (ii) deoxynivalenol, an *E. coli* mycotoxin, paired with an scFv binding thereto and described at Protein Expr. Purif. 35 (1): 84-92; (iii) HPV-16 protein E5, paired with an antibody thereto described at Biomed. Res. Int. 2018; 2018:5809028; (iv) a rabies virus protein and an scFv binding thereto and described at Protein Expression and Purification 86 (2012) 75-81; (v) an influenza A matrix protein paired with an scFv binding thereto and described at Bioconjugate Chem. 2010, 21, 1134-1141; (vi) amino acids 134-145 (PRVRGLYFPAGG, SEQ ID NO:3) of pre-S2 protein of HBV, paired with an scFv binding thereto and described at Viral Immunol. 2018 May 30; (vii) a VP 3 peptide of duck hepatitis virus type 1, paired with an scFv described at J. of Virological Methods 257 (2018) 73-78; (viii) a peptide (MEESKGYEPP, SEQ ID NO:4) from Glycoprotein D of bovine herpes virus 1 paired with an scFv described at Appl Microbiol Biotechnol. 2017 December; 101 (23-24): 8331-8344; (ix) a peptide comprising amino acid 159 of VP1 protein of South African Territories 2 (SAT2) foot and mouth virus, paired with an scFv binding thereto and described at Virus Research 167 (2012) 370-379; (x) a peptide (DRTNNQVKA, SEQ ID NO:5) of OmpD from *Salmonella typhimurium*, paired with an scFv binding thereto and described at Veterinary Microbiology 147 (2011) 162-169; (xi) a peptide of isoferritin from *E. coli*, paired with an scFv binding thereto and described at Journal of Biotechnology 102 (2003) 177/189; (xii) a peptide (AQEPPRQ, SEQ ID NO:6) located at the N terminus of the grapevine leafroll-associated virus 3 coat protein, paired with an scFv binding thereto an described at Arch. Virol. (2008) 153:1075-1084; (xiii) a peptide (PTDSTDNNQNGGRNGARPKQRRPQ, SEQ ID NO:7) of N protein of SARS-COV, paired with an scFv binding thereto and described at Acta Biochimica et Biophysica *Sinica* 2004, 36 (8): 541-547; (xiv) a peptide containing amino acids 1-15 of HIV Tat protein, paired with an scFv that binds thereto and is described at J. Virol. 2004 April; 78 (7): 3792-3796; and (xv) a peptide from amino acids 1363-1454 of the helicase domain of HCV NS3, paired with an scFv binding thereto and described at J. Hepatology 37 (2002) 660-668, J Virol 1994; 68:4829-4836, and Arch Virol 1997; 142:601-610.

Other examples of universal CARs that can be paired with an aptameric bridge of the present technology are described at J. Autoimmun. 2013 May. 42:105-16; Blood Cancer J. 2016 Aug. 6 (8): e458; Oncotarget. 2017 Dec. 12, 8 (65): 108584-108603; Oncotarget 2017 May 9, 8 (19): 31368-31385; Oncotarget 2018 Jan. 26, 9 (7): 7487-7500; and WO2016030414.

The linking moiety of an aptameric bridge can be simply one or more covalent bonds between individual aptamers, or can be a synthetic or naturally occurring polymer such as a hydrocarbon, polyether, polyamine, polyamide, nucleic acid, peptide, carbohydrate, or lipid. In certain embodiments, the linking moiety is not a peptide. In certain embodiments, the aptameric bridge is devoid of peptides, and is devoid of polypeptides and proteins. The linking moiety also can take the form of a nanoscale structure (such as a polymer, protein, nanoparticle, nanotube, nanocrystal, nanowire, nanoribbon, nanocrystal, micelle, or liposome), or a microscale structure (such as a microbead or a cell), or a larger structure (such as a solid support). Preferably, the linking moiety is a biodegradable polymer. The linking moiety can be a polymer that is linear, branched, cyclic, or a combination of these structures. The linking moiety can also serve as the backbone for a dendrimeric structure, or a hub or star-shaped structure (such as a core structure to which two or more aptamers are bound). For non-covalent association, two or more individual aptamers can be bound via non-covalent interactions either directly between the aptamers or through interaction with a linking moiety. The non-covalent interactions can be, for example, one or more hydrogen bonds, ionic bonds, hydrophobic bonds, van der Waals interactions, or a combination thereof. High affinity binding pairs, such as streptavidin-biotin, can be used to non-covalently link aptamers in an aptameric bridge.

A linker or linking moiety can be any chemical moiety that covalently or non-covalently joins monomeric aptamer units together. The linker can include or consist of, for example, oligonucleotides, polynucleotides, peptides, polypeptides, or carbohydrates. The linker can include or consist of a cell receptor, a ligand, or a lipid. The linker can include or consist of a hydrocarbon chain or polymer such as a substituted or unsubstituted alkyl chain or ring structure, a polyethylene glycol polymer, or a modified or unmodified oligonucleotide or polynucleotide. The linker can be a single covalent bond, or can include one or more ionic bonds, hydrogen bonds, hydrophobic bonds, or van der Waals interactions. The linker can include a disulfide-bridge, a heparin or heparan sulfate-derived oligosaccharide (a glycosoaminoglycan), a chemical cross-linker, hydrazone, thioether, ester, or triazole. The linker can be cleavable by an enzyme, allowing for release of individual aptamers and/or termination of a CAR-target interaction by the aptameric bridge. The linker can have a net positive, negative, or neutral charge. The linker can be as flexible or as rigid as desired to ensure preservation of the functional properties of the individual monomeric aptamers units in a multimeric construct and to promote binding to the CAR and target, or to promote their interaction. The linker can include a flexible portion, such as a polymer of 5-20 glycine and/or serine residues. The linker can also contain a rigid, defined structure, such as a polymer of glutamate, alanine, lysine, and/or leucine. The linker can include a hinge portion or a spacer portion. The linker can include a substituted or unsubstituted $C_2$-$C_{50}$ chain or ring structure, a polyethylene glycol polymer (e.g., hexaethyleneglycol), or a modified or unmodified oligonucleotide or polynucleotide. The linker can include a heparin or heparan sulfate-derived oligosaccharide (a glycosoaminoglycan), a chemical cross-linker, peptide, polypeptide, hydrazone, thioether, or ester.

A $C_2$-$C_{50}$ linker can include a backbone of 2 to 50 carbon atoms (saturated or unsaturated, straight chain, branched, or cyclic), 0 to 10 aryl groups, 0 to 10 heteroaryl groups, and 0 to 10 heterocyclic groups, optionally containing an ether linkage, (e.g., one or more alkylene glycol units, including but not limited to one or more ethylene glycol units —O—($CH_2CH_2O$)—; one or more 1,3-propane diol units; an amine, an amide; or a thioether. Each backbone carbon atom can be independently unsubstituted (i.e., comprising only-H substituents) or can be substituted with one or more groups selected from $C_1$ to $C_3$ alkyl, —OH, —$NH_2$, —SH, —O—($C_1$ to $C_6$ alkyl), —S—($C_1$ to $C_6$ alkyl), halogen, —OC(O) ($C_1$ to $C_6$ alkyl), and —NH—($C_1$ to $C_6$ alkyl). In some embodiments, the linker is a $C_2$-$C_{20}$ linker, a $C_2$-$C_{10}$ linker, a $C_2$-$C_8$ linker, a $C_2$-$C_6$ linker, a $C_2$-$C_5$ linker, a $C_2$-$C_4$ linker, or a $C_3$ linker, wherein each carbon may be independently substituted as described above.

In certain embodiments, there is non-covalent bonding between aptamers, mediated for example through ionic bonding, hydrogen bonding, hydrophobic bonding, van der Waals interactions, or a mixture thereof, without any intervening linking moiety joining the individual aptamers. A single multimeric aptamer construct also can use a mixture of covalent bonding, through an intervening linker moiety connecting certain apamers, and non-covalent bonding, without an intervening linker moiety, at other bonding sites between aptamers.

The linkers optionally can have one or more functionalities. For example, in some embodiments, the linker is sensitive to temperature and/or pH, meaning that the linker either changes conformation or is cleaved at a pre-designed range of temperature and/or pH.

Each of the CAR-binding portion and the target-binding portion of an aptameric bridge can include single aptamers, or can include two or more identical or non-identical aptamer units. The use of two or more identical aptamers, or aptamers which are non-identical but bind to the same target, can have greatly enhanced binding affinity through cooperativity of binding or binding of the same target presented differently, particularly for targets, such as cells, that possess multiple copies of a given target molecule. Identical monomeric aptamers can have completely identical nucleotide sequences, (100% identical), or they can have sequences that are about 99% identical, about 98% identical, about 97% identical, about 96% identical, about 95% identical, about 94% identical, about 93% identical, about 92% identical, about 91% identical, or about 90% identical, or at least 70%, at least 80%, at least 85%, at least 90%, at least 95%, at least 97%, at least 98%, or at least 99% identical.

Each of the CAR-binding portion and the target-binding portion of an aptameric bridge can include two or more individual aptamers that are non-identical and bind to the same or different targets. The non-identical aptamers can differ in structure, nucleotide sequence, and/or binding specificity or binding affinity. Such a bridge can specifically bind to two or more different sites on the target, such as different epitopes of a protein or different surface proteins of a target cell, or different CARS, thereby increasing affinity and/or specificity for the target, or binding to different target cells and/or different CAR-expressing cells. The different targets or different CARS can be chosen so as to maximize the desired therapeutic effect, through a combination of actions involving different target cells and/or different CAR-expressing cells.

The function of CAR cells may be improved by directing them to two or more antigens on target cells, e.g., to two or more antigens on a given tumor cell, such as CD19 and CD22, CD19 and CD123, or CD19 and BCMA. Such an approach could help to overcome tumor antigen loss and achieve improved durability of response. An aptameric bridge can be engineered to recognize the CAR and two or more antigens on the same target cell by linking two or more aptamers together in the target-binding portion. This approach would be similar to engineering T cells to express two tumor associated antigen receptors at the same time, but extending beyond the dual target limitation of antibodies and providing lower cost and greater flexibility than antibody-based CAR switches.

The aptameric bridge constructs of the present technology can be used in an immunotherapeutic composition. An embodiment of such a composition includes the aptameric bridge and an excipient. The aptameric bridge can be associated with other molecules, or with structures such as liposomes, micro- or nanoparticles, receptor- or cell-targeted molecules, or oral, topical or other formulations for assisting in uptake, distribution and/or absorption. In some embodiments, the aptameric bridge is encapsulated, conjugated, or otherwise associated with a therapeutic agent delivery vehicle. In some embodiments, the therapeutic agent delivery vehicle is a gene delivery vehicle, such as a viral vector, or includes a viral vector. The viral vector can be any type of suitable vector, such as an expression vector or a plasmid. In preferred embodiments, the vector is a lentiviral vector. In preferred embodiments, the CAR-encoding vector is administered to the subject first, and an initial baseline of CAR expression, and in some embodiments CAR cell expansion, is established in the subject prior to administering an aptameric bridge to the subject to activate an immune response against the target. CAR expression, and optionally expansion of CAR-expressing cells, can be detected and/or quantified in the subject, for example, by administering a CAR-binding aptamer (such as the CAR-binding portion of the aptameric bridge) in a labeled form, followed by determining bound label in peripheral blood cells or determining the distribution of label in the body.

The component aptamers of an aptameric bridge can include any desired modifications to aptamer structure or sequence. The modifications can include substitutions introduced in one or more ribose or deoxyribose moieties of a candidate aptamer. The modifications can include substitutions in one or more phosphate moieties of a candidate sequence. The modifications can include substitutions in one or more purine or pyrimidine moieties of a candidate aptamer, or substituting unnatural or rare natural nucleotides for natural nucleotides of a candidate aptamer. Chemical modifications can be introduced into internucleotide phosphate bonds, such as replacement of internucleotide phosphates with phosphorothioates or boranophosphates, addition of biotine, azide or alkine groups. Chemical modifications can be introduced at the C2' position of the ribose ring, such as introduction of fluorine, LNA (locked nucleic acid) units, or 2'-O-alkyl modifications. One or more nucleosides of an aptamer can include a modification selected from a 2'-position sugar modification (such as a 2'-amino (2'—$NH_2$), a 2'-fluoro (2'-F), or a 2'-O-methyl (2'-OMe)), a modification at a cytosine exocyclic amine, an internucleoside linkage modification, or a 5-methyl-cytosine. The aptamer can include a 3' cap, a 5' cap, and/or an inverted deoxythymidine at the 3' terminus. Rare nucleotides such as 2-thiouridine (s2U), pseudouridine (Y), and dihydrouridine (D), or unnatural nucleotides such as peptide nucleic acids (PNA), morpholino, locked nucleic acids (LNA), glycol nucleic acids (GNA), or threose nucleic acids (TNA) can substitute for commonly occurring nucleotides. Unnatural nucleic acids (xeno nucleic acid (XNA)) also can be included.

Any suitable method for making or selecting an aptamer to a target can be employed to obtain the component aptamers of an aptameric bridge. For example, aptamers can be identified by Systematic Evolution of Ligands by Exponential Enrichment (SELEX). SELEX is described, for example, in U.S. Pat. No. 5,270,163 which is hereby incorporated by reference. Briefly, SELEX starts with a plurality of nucleic acids (i.e., candidate aptamer sequences) containing varied nucleotide sequences which are contacted with a target. Unbound nucleic acids are separated from those that form aptamer-target complexes. The aptamer-target complexes are then dissociated, the nucleic acids are amplified, and the steps of binding, separating, dissociating, and amplifying are repeated through as many cycles as desired to yield a population of aptamers of progressively higher affinity to the target. Cycles of selection and amplification can be repeated until no significant improvement in binding affinity is achieved on further repetitions of the cycle.

The cycles of selection and amplification can be interrupted before a single aptamer is identified. In such cases, a population of aptamers is identified, which can offer significant information regarding the sequence, structure, or motifs that allow binding of the aptamer with a target. Such a population of candidate aptamers also can inform which portions of the aptamer are not critical for target binding. This information can then guide the generation of other aptamers to the same target. The aptamers thus generated can be used as input for a new round of SELEX, potentially yielding aptamers with better binding affinities or other characteristics of interest.

In some embodiments, candidate aptamer sequences are created that contain multimeric aptamer constructs, such as candidate aptameric bridges, which are then subjected to further rounds of selection as a multimeric construct. Multimeric candidate aptamer constructs can be made by linking individual candidate aptamer moieties with a linking moiety, and optionally using such constructs as input for one or more rounds of SELEX. In some embodiments, individual aptamers are independently selected via one or more rounds of SELEX, and finally linked together with a linking moiety. Therefore, multimerization of monomeric aptamers as well as of multimeric aptamer constructs can be performed prior to, during, or post SELEX procedures.

For selecting the component aptamers of an aptameric bridge, selection may be performed differently for aptamers that bind a CAR compared to aptamers that bind a target on a target cell. The selection of aptamers that bind the target cell can be performed by associating candidate aptamers with an intact target cell, recombinant cell, pathogen cell, virus-like particle, or purified target protein or peptide epitope, or with a membrane preparation from a target cell, or recombinant cell containing an antigenic surface protein. However, selection of aptamers that bind an anti-PNE CAR can be performed by contacting candidate aptamers with the anti-PNE CAR expressed on a cell in the presence and absence of the PNE. Thus, according to this method, aptamers having the desired binding affinity for an anti-PNE CAR will be those whose binding to the CAR in the absence of the PNE can be displaced by adding a peptide containing the PNE. However, aptamers also can be selected using peptides from regions of the CAR different from, such as adjacent to, the PNE binding site, and aptamers selected in this manner might not be displaced by the PNE yet could offer high affinity binding for the anti-PNE CAR. Further, in order to promote a successful immunotherapy, the activation of CAR-expressing cell, such as a T cell expressing the CAR, should be monitored during the aptamer selection process. For this purpose, selection of candidate CAR-binding aptamers can be performed using the candidate CAR-binding aptamers installed into an aptameric switch, together with candidate target binding aptamers.

The component aptamers of an aptameric bridge can have any desired length. In some embodiments, a component aptamer includes at least about 15 nucleotides. In some embodiments, the component aptamer includes up to about 100 nucleotides. The length of the aptameric bridge can determine the distance between cells interacting through the bridge. As such, the length of the bridge is preferably in the range from about 70 to about 200 angstroms, or about 70 to about 150 angstroms, or about 100 to about 170 angstroms, or about 120 to about 150 angstroms.

Techniques can be used to identify or generate aptamers with any desired binding affinity. In preferred embodiments, the one or more selected aptamers have a $K_d$ for binding to the target of from about 1 pM to about 10 nM for high affinity (specific) binding, or from about 100 nM to about 10 UM for low affinity binding. In some embodiments, the aptamer has a $K_d$ of about 1 pM up to about 10 UM; about 1 pM up to about 1 µM; about 1 pM up to about 100 nM; about 100 pM up to about 10 µM; about 100 pM up to about 1 µM; about 100 pM up to about 100 nM; or about 1 nM up to about 10 µM; about 1 nM up to about 1 µM; about 1 nM up to about 200 nM; about 1 nM up to about 100 nM; about 500 nM up to about 10 UM; or about 500 nM up to about 1 µM. In some embodiments, the binding affinity of a component aptamer within an aptameric bridge is 4 to 50 times higher than the affinity of the monomeric candidate aptamer. In some embodiments, the affinity of component aptamers of an aptameric bridge to one or more targets can be fine-tuned by altering the degree of multimerization within the bridge, the component aptamers included in the bridge, or the linker. In certain embodiments, the CAR-binding portion and/or the target-binding portion of the bridge is multivalent, meaning that it contains two or more individual aptamers that bind the same or different sites on the CAR or target. Multivalent aptamer constructs offer the advantages of greater binding specificity and/or higher binding affinity for the CAR or the target. The binding affinity of multimeric aptamers can be much higher than for single aptamers because binding of the multimeric complex can exhibit positive cooperativity or positive allosterism among the individual binding sites. The ability to carefully select and combine binding sites in a multimeric aptamer bridge portion increases safety profile by limiting harmful or toxic effects and enhancing effective treatment effects.

In some embodiments, the aptamers of an aptameric bridge are stabilized and/or multimerized by complexation with another compound, such as biotin-avidin or polyethylene glycol. In some embodiments, aptamers are synthesized utilizing a solid support.

The aptameric bridges disclosed herein are useful for preventing or treating proliferative or infectious diseases. One aspect of the present invention is a method of preventing or treating cancer or infection by administering an aptameric bridge or an immunotherapeutic formulation or a therapeutic agent delivery vehicle including an aptameric bridge.

The invention also provides a method of inducing or enhancing an immune response against a cancer or an infectious disease in a subject by administering an aptameric bridge or an immunotherapeutic formulation or a therapeutic agent delivery vehicle including an aptameric bridge.

The invention further provides a method of specifically associating an immune cell expressing a CAR with a target cell against which an immune response or an enhanced immune response is desired. Administering an aptameric bridge having binding specificity for both the CAR and a molecular target on the target cell leads to activation of the CAR-expressing immune cell and initiation or enhancement of an immune response against the target cell.

EXAMPLES

Example 1. Preparation of Bispecific Aptamers Specific for PSMA and CD3

A10 RNA aptamer (SEQ ID NO:8) is a 39 nucleotide-long sequence that has been selected against the human prostate-specific membrane antigen (PSMA) and used as a prostate specific delivery agent for siRNA (McNamara et al. 2006-Dassie et al. 2009).

CELTIC_1s, CELTIC_19s and CELTIC_core are DNA aptamers (SEQ ID NOS: 9, 10 and 11), and ARACD3-3700006 and ARACD3-0010209 are RNA aptamers (SEQ ID NOS: 12 and 13), that have all been previously selected against human CD3. These DNA or 2'-Deoxy-2'-fluoro-thymidine-modified RNA (2'F-RNA) aptamers were purchased from baseclick (Neuried, Germany) as HPLC-RP purified single stranded oligos synthetized via standard solid phase phosphoramidite chemistry. The anti-CD3 aptamers did not activate cytokine secretion or surface marker expression even when combined with costimulatory anti-CD28 antibody, and unlike anti-CD3 monoclonal antibodies (data not shown).

Figure 7A:
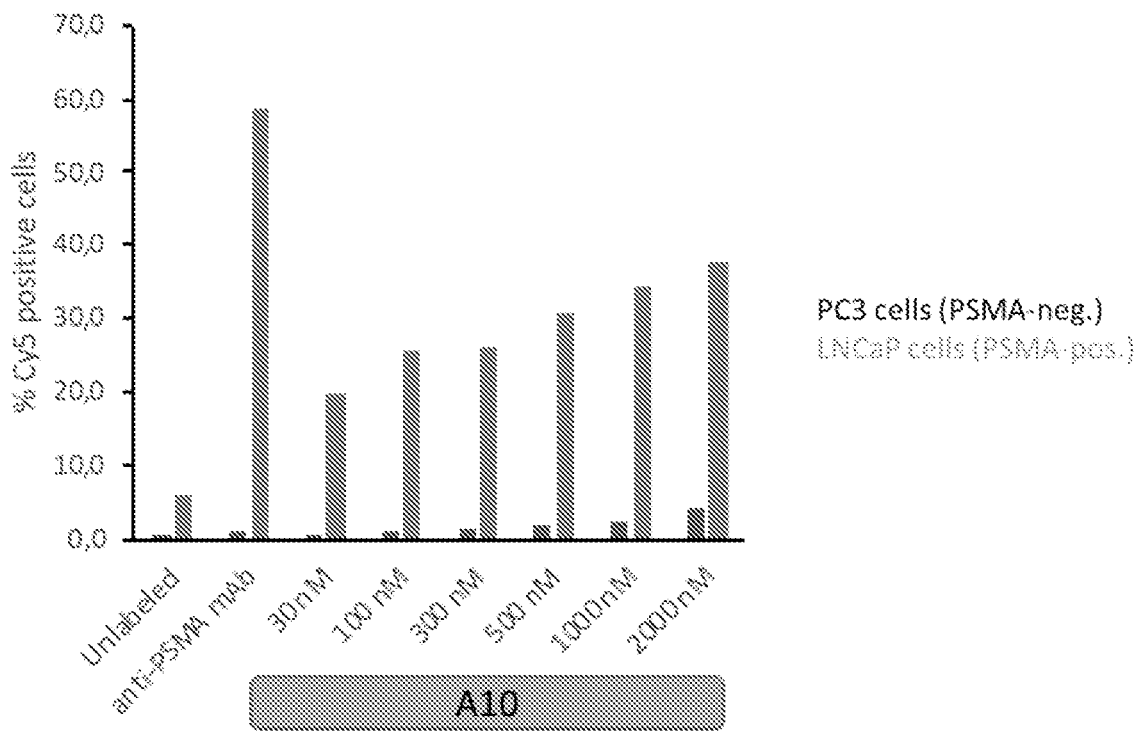
FIGS. 7A and 7B show binding of anti-PSMA (7A) and anti-CD3 (7B) aptamers to cells that do and do not express the respective antigens.
Figure 7B:
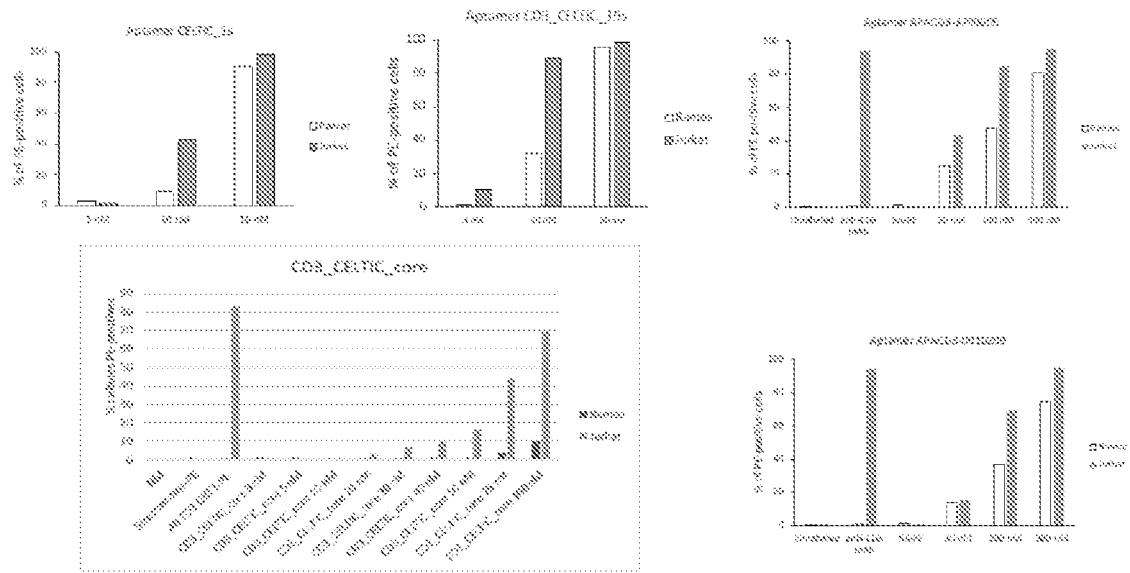

A10 aptamer was modified with an azide group at its 3'-end for subsequent triazole inter-nucleotide dimerization. Biotin was added to the 5'-end of A10 aptamer as a Biotin-TEG that introduces a 16-atom mixed polarity spacer between the aptamer sequence and the biotin flag. A Cy5-labelled version of A10 was also synthetized. CELTIC_1s, CELTIC_19s, CELTIC_core, ARACD3-3700006 and ARACD3-0010209 were modified with an alkyne group at their 5'-end for subsequent triazole inter-nucleotide dimerization. Molecular weight, purity and integrity were verified by HPLC-MS. Affinity and specificity of the A10 anti-PSMA RNA aptamer was evaluated on PSMA positive and PSMA negative cells (FIG. 7A).

Figure 8A:
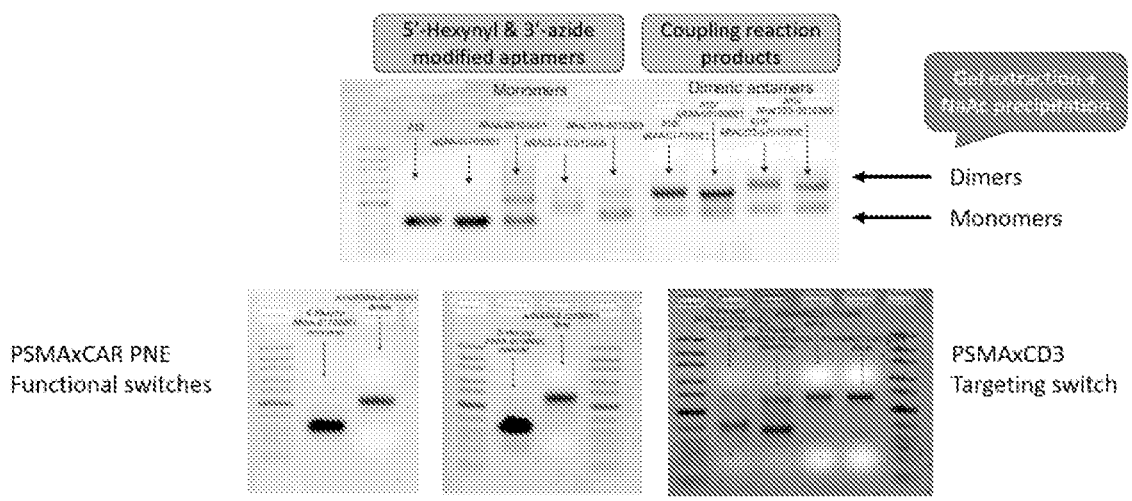
FIGS. 8A and 8B show agarose gels of monomeric and dimeric (bispecific) aptamers.
Figure 8B:
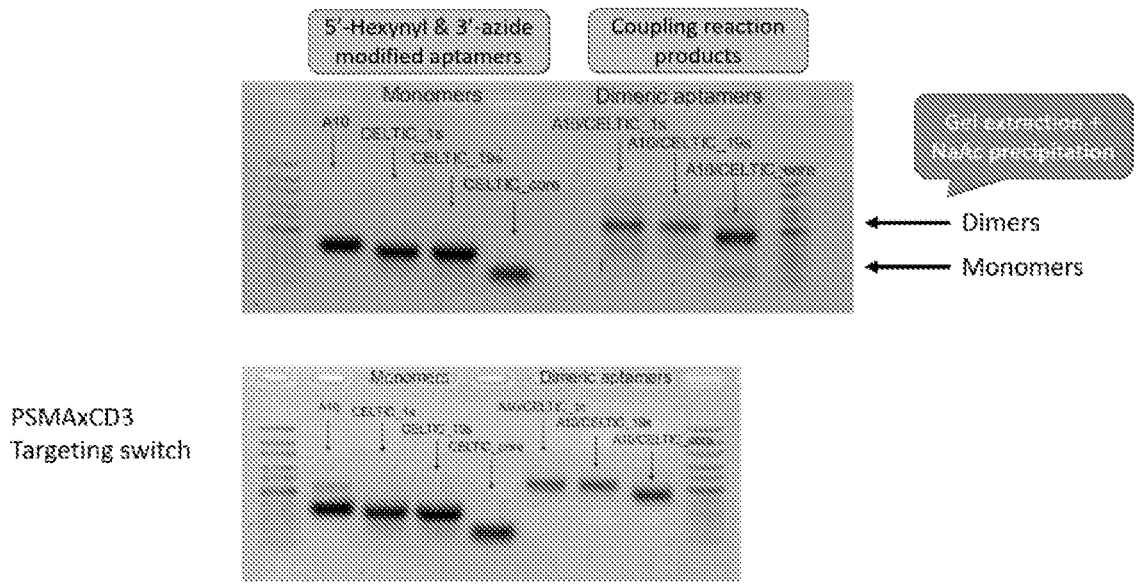

Anti-PSMA A10 and anti-CD3 aptamers were heterodimerized by copper-catalyzed click reaction performed for 60 min at 45° C. with the Oligo2-Click kit L (baseclick, Neuried, Germany) according to manufacturer's instructions. Reaction products were separated by gel electrophoresis on 3% agarose gel migrated in 1×TBE buffer (Invitrogen) at 100 V during 30 min. The gels were visualized using Bio-Rad imaging system and the results are shown in FIGS. 8A and 8B. Gel slices corresponding to dimeric aptamers were cut out from the gel and nucleic acids were extracted for 72 h at 8° C. by passive elution in 25 mM NaCl-TE buffer. Bispecific aptamer dimers were recovered by standard sodium acetate precipitation, resuspended in sterile water and stored at −20° C. until use.

Example 2. Functional Stability of Aptamer A10 Specific for PSMA

Figure 9:
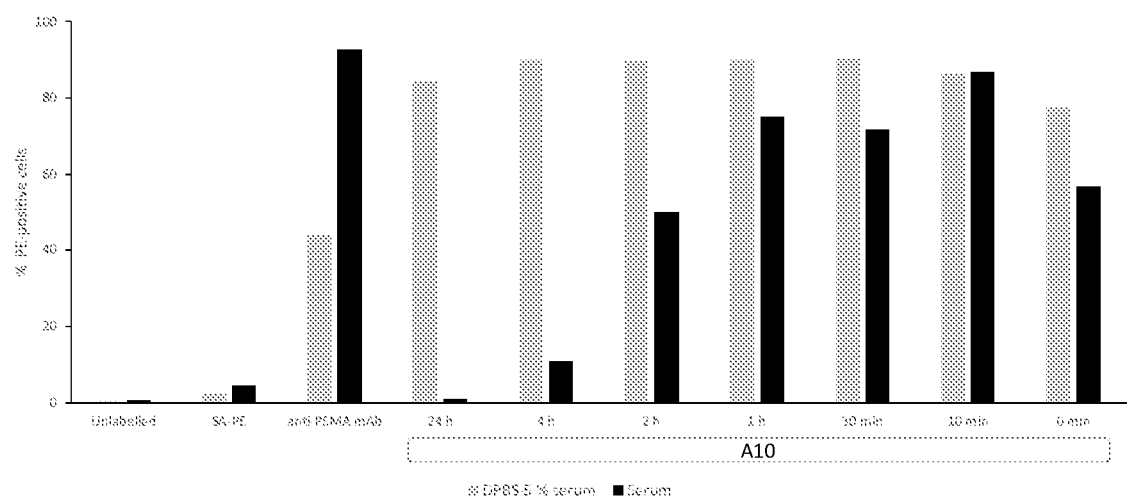
FIG. 9 shows the time course of an RNA aptamer in serum.

Stability of A10 RNA aptamer was measured in Dulbecco's phosphate-buffered saline (DPBS) containing 5% FBS or the FBS alone. Biotinylated aptamer was denatured at 85° C. for 5 min and then immediately cooled on ice block to 4° C. for 5 min. The aptamer was then diluted to a final concentration of 2 µM in DPBS supplemented with 5% of FBS or in pure FBS. Samples were incubated at 37° C. for 10 min, 30 min, 1 h, 2 h, 4 h or 24 h; the control sample contained the freshly prepared aptamers without incubation at 37° C. 100 nM streptavidin-PE was then added to each solution and aptamer was incubated with PSMA-positive LNCaP cells (Human Prostate Carcinoma-ATCC CRL-1740). The half-life of aptamer A10 in DPBS buffer containing 5% FBS or in pure FBS was then determined using flow cytometry on the YL-1 channel, based on the variation of the fluorescence-positives cells number as a function of the incubation time at 37° C. The results of the measurements are shown in FIG. 9. Aptamer A10 incubated in DPBS buffer containing 5% serum was stable over 24 h. When tested in pure serum, half of the binding activity was lost within the first 2 h of incubation.

Example 3. Determination of the Affinity and Specificity of Anti-PSMA×Anti-CD3 Bispecific Aptamer to Targets Expressed on Cells The affinity and specificity of anti-PSMA×anti-CD3 bispecific aptamers to target proteins expressed on cells were evaluated by flow cytometry. These studies were performed on CD3-positive Jurkat (Acute T Cell Leukemia Human Cell Line-ATCC TIB-152), CD3-negative Ramos (Burkitt's Lymphoma Human Cell Line-ATCC CRL-1596), PSMA-positive LNCaP (Human Prostate Carcinoma-ATCC CRL-1740) and PSMA-negative PC-3 (Human Prostate Carcinoma-ATCC CRL-1435) cells by incubation with biotinylated RNA/DNA aptamers in SELEX buffer or RNA/RNA aptamers in DPBS buffer, supplemented with 5% of FBS. Cells were cultured in RPMI-1640 medium (Gibco Invitrogen), supplemented with 10% FBS (Gibco Invitrogen) and 1% Penicillin/Streptomycin (Gibco Invitrogen) prior to use. Prior to experiment, Jurkat, Ramos, LNCaP and PC-3 cells ($2.5 \times 10^5$ cells/well) were seeded in 96-well plates and centrifuged at 2500 rpm for 2 min. The supernatant was discarded, and the pelleted cells were washed twice with 200 µL of SELEX or DPBS-5% FBS buffer preheated at 37° C. Each washing step was followed by centrifugation at 2500 rpm for 2 min. Aptamers were denatured at 85° C. for 5 min and immediately placed on ice block of 4° C. for 5 min. Test samples were subsequently diluted at two different concentration ranges: 3, 10, 30,100 and 300 nM (CD3 binding assays) and 30, 100 and 300 nM (PSMA binding assays) followed by addition of 100 nM phycoerythrin-labelled streptavidin (streptavidin-PE, eBioscience) to each solution. Jurkat, Ramos, LNCaP and PC-3 cells were resuspended in the aptamer dilutions (100 µL/well) and incubated at 37° C. for 30 min in a 5% $CO_2$ humidified atmosphere. As controls, cells were incubated with CD3 monoclonal antibodies (PE-labelled, OKT3 human anti-CD3, Invitrogen), PSMA monoclonal antibodies (Alexa Fluor 488-labelled, GCP-05 human anti-PSMA, Invitrogen), PE-streptavidin or the respective buffers without additional reagents. After incubation, cells were centrifuged at 2500 rpm for 2 min and the supernatant with unbound sequences was discarded. The pelleted cells were washed with SELEX or DPBS-5% FBS buffer (200 µL/well) and centrifuged twice in order to remove all weakly and non-specifically attached sequences. The cells were then washed with 1 mg/mL salmon sperm DNA solution (100 µL/well) at 37° C. in a 5% $CO_2$ humidified atmosphere. After 30 min, the salmon sperm solution was removed by centrifugation at 2500 rpm for 2 min and the cells were additionally washed twice with SELEX or DPBS-5% buffer (200 µL/well) followed by centrifugation. Jurkat, Ramos, LNCaP and PC-3 cells with attached DNA or RNA sequences were then fixed (BD CellFIX solution #340181) and the fluorescence-positive cells were counted by flow cytometry (AttuneNXT; Invitrogen, Inc.) on the YL-1 channel.

Figure 10A:
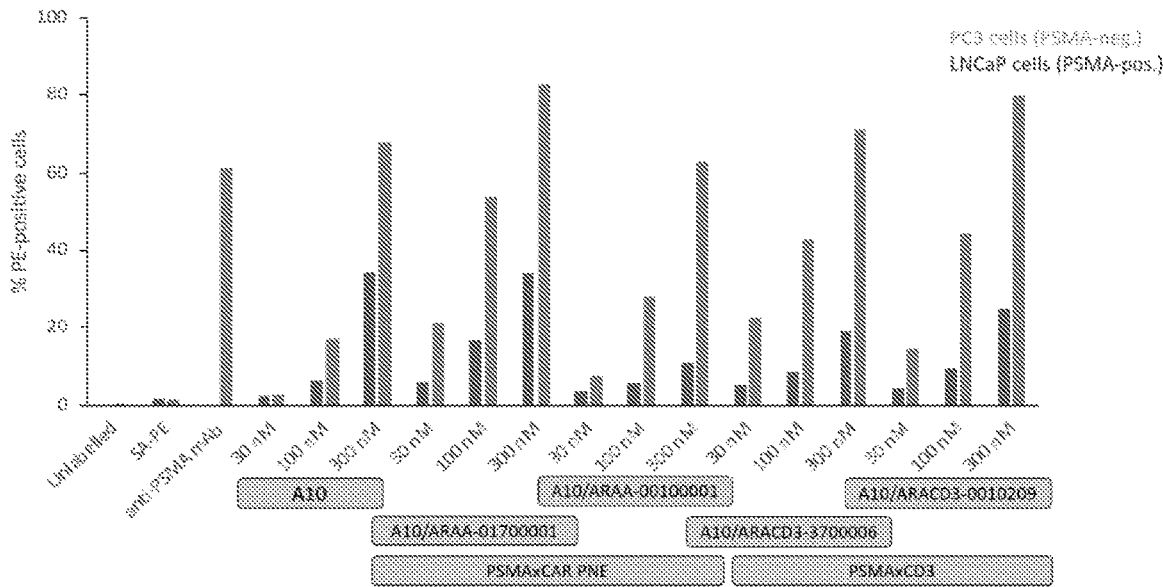
FIGS. 10A and 10B show the binding affinities of bispecific aptamers to PSMA-positive and negative cells.
Figure 10B:
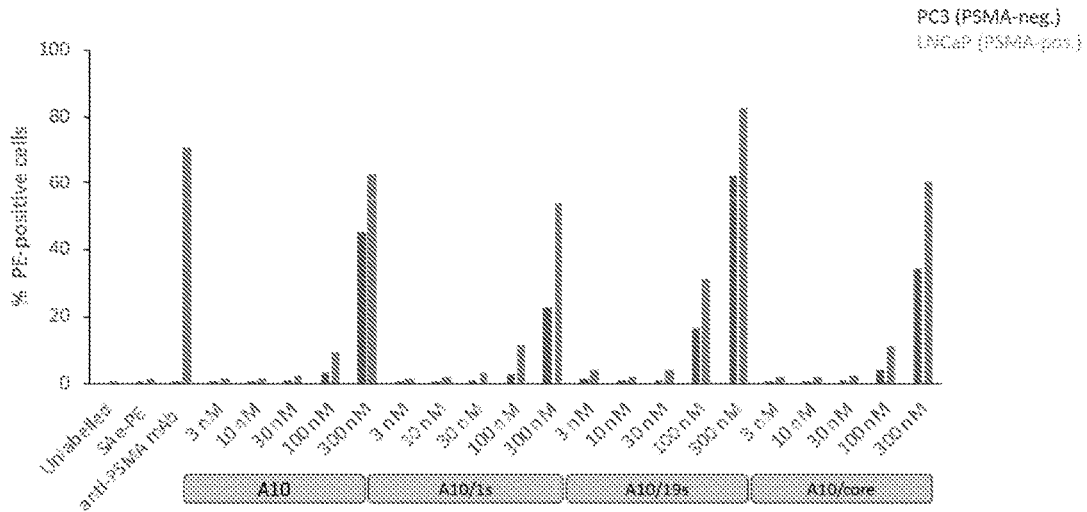

The results of the binding studies to PSMA-positive cells are shown in FIGS. 10A and 10B. Three RNA/DNA aptamers (A10×CELTIC_1s, A10×CELTIC_19s, A10×CELTIC_core) and two RNA/RNA aptamers (A10×ARACD3-3700006 and A10×ARACD3-0010209) were analyzed along with A10 monomeric aptamer. For comparison, binding of the tested reagents to PSMA-negative PC-3 cells was also measured. A dose-dependent binding to PSMA-positive LNCaP cells was observed with A10 without reaching saturation of the signal at the highest tested concentrations. Intensity of the signal was as strong as for the antibody control. Residual binding of A10 monomer to PC-3 cells was only observed at the highest tested concentration. All bispecific PSMA×CD3 aptamers exhibited similar binding properties to A10 monomer but with an improved specificity for target-positive cells as residual binding to PSMA-negative cells was reduced. For each tested concentration, signal intensity of bispecific aptamers was superior to the one measured for A10 monomer, suggesting that heterodimerization resulted in an improvement of the affinity.

Figure 11A:
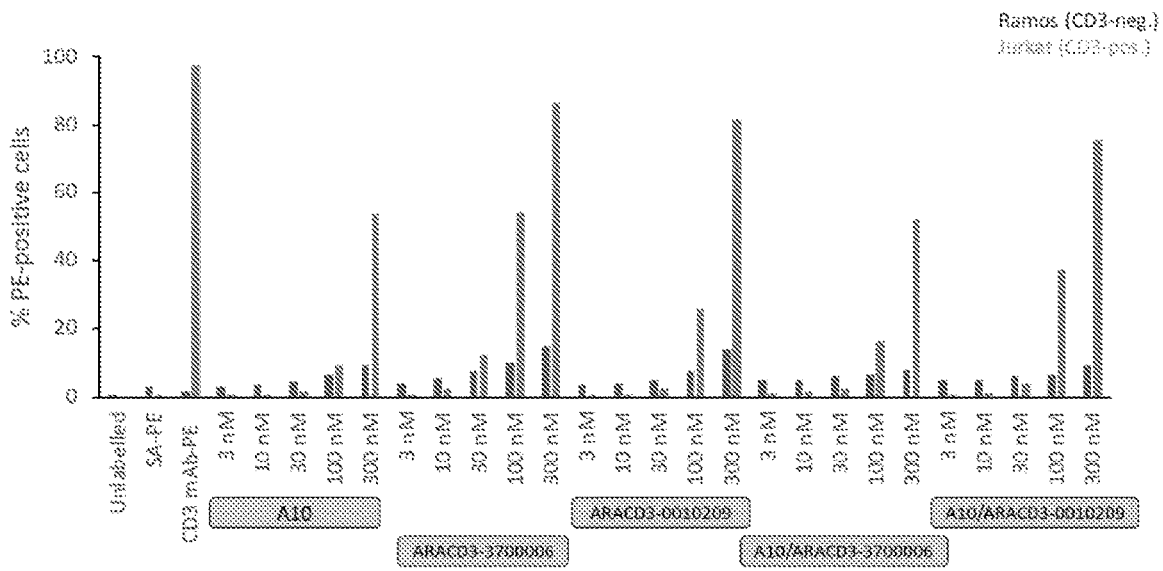
FIGS. 11A and 11B show the binding affinities of bispecific aptamers to CD3-positive and negative cells.
Figure 11B:
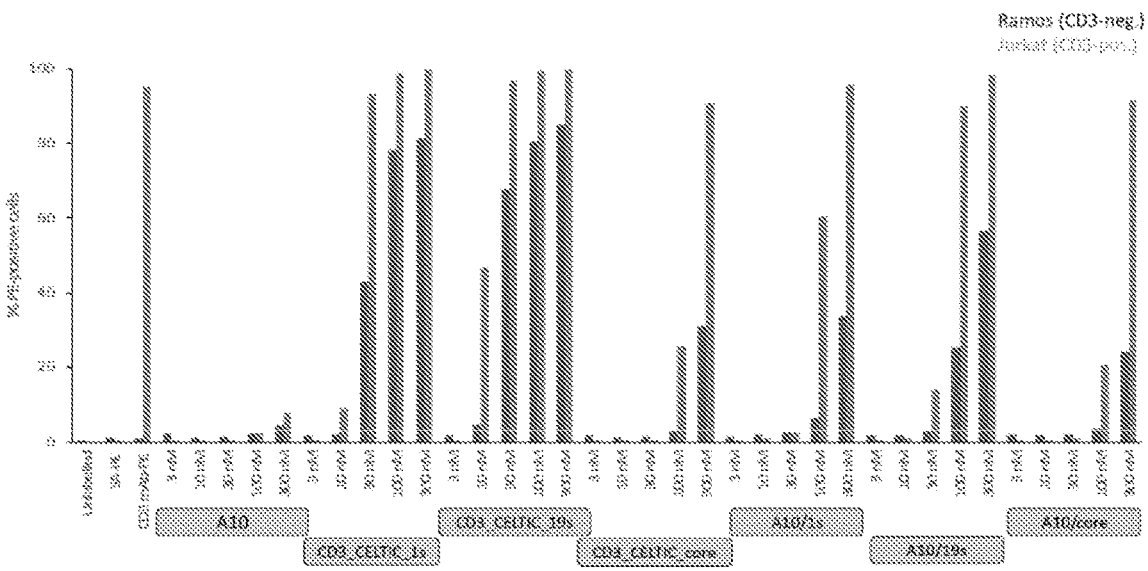

In another experiment, binding of the same aptamers to CD3-positive Jurkat and CD-3 negative Ramos cells was investigated. See FIGS. 11A and 11B. As expected A10 aptamer did not bind to these two cell lines. Residual binding of anti-CD3 monomers to Ramos cells was only observed at the highest tested concentration. All bispecific PSMA×CD3 aptamers exhibited similar dose-dependent binding but with superior specificity for target-positive cells as residual binding to CD3-negative cells was strongly reduced. For each tested concentration, signal intensity of bispecific aptamers was inferior to the one measured for anti-CD3 monomers, suggesting that heterodimerization resulted in the lowering of the affinity.

Altogether, these results suggest that after heterodimerization the binding properties of aptamers selected against different targets are not destroyed due to steric hindrance when evaluated separately. Depending on the selected partners, specificity and affinity for respective targets may even be improved upon dimerization.

Example 4. Binding of Bispecific Aptamers Targeting PSMA and CD3 as Measured by Surface Plasmon Resonance Binding affinity measurements were performed using a BIAcore T200 instrument (GE Healthcare). To analyze interactions between aptamers and CD3 and PSMA proteins, 300 Resonance Units of biotinylated aptamers were immobilized on Series S Sensor chips SA (GE Healthcare) according to manufacturer's instructions (GE Healthcare). DPBS buffer was used as the running buffer. The interactions were measured in the "Single Kinetics Cycle" mode at a flow rate of 30 µl/min and by injecting different concentrations of human CD3 ε/γ, CD3 ε/δ, IgG1 Fc and PSMA (Acro Biosystems). The highest aptamer concentration used was 300 nM. Other concentrations were obtained by 3-fold dilution. All kinetic data of the interaction were evaluated using the BIAcore T200 evaluation software.

Comparison of $K_D$ values for monomeric and bispecific aptamers shows that dimerization does not disturb binding properties of each subunit for its particular target. Simultaneous binding of PSMA and CD3 ε/γ also can be recorded with the manual injection mode at a flow rate of 10 µl/min and by injecting a solution of the first target at a saturating concentration followed by a solution of the second target at a saturating concentration. A second injection with an inverted sequence is performed. In both sequences, each injection resulting in responses of equal intensities indicates that both arms of bispecific aptamers are able to bind the second target while the binding site for the first antigen is occupied. Monomers failing to respond to both injections of target solutions indicate that the bispecific aptamer can simultaneously bind both targets.

Example 5. Bioactivity of Bispecific Aptamers Specific for PSMA and CD3

Cytotoxicity assays were carried out on unstimulated peripheral blood mononuclear cells (PBMCs). Freshly prepared PBMCs were isolated from buffy coats obtained from healthy donors (Etablissement Français du Sang, Division Rhônes-Alpes). After diluting the blood with DPBS, the PBMCs were separated over a FICOLL density gradient (FICOLL-PAQUE PREMIUM 1.077 GE Healthcare), washed twice with DPBS, resuspended in RPMI-1640 medium (Gibco Invitrogen) to obtain a cell density of $5 \times 10^6$ cells/ml. These PBMCs were used as effector cells.

LNCaP target cells were labeled with 2 µM calcein AM (Trevigen Inc, Gaithersburg, MD, USA) for 30 min at 37° C. in cell culture medium. The calcein AM fluorochrome is a dye that is trapped inside live LNCaP cells and only released upon redirected lysis. After 2 washes in cell culture medium, a cell density of $5 \times 10^5$ cells/ml was adjusted in RPMI-1640 medium and 100 µl aliquots of 50,000 cells were used per assay reaction. A standard reaction at 37° C./5% $CO_2$ lasted for 4 hr and used $5 \times 10^4$ cells calcein AM-labeled target cells, $5 \times 10^5$ PBMCs (E/T ratio of 1:10) and 20 µl of bispecific aptamer solutions at 1 µM in a total volume of 200 µl. After the cytotoxic reaction, the released dye in the incubation medium was quantitated in a fluorescence reader (VarioSkan Lux, ThermoFisher, Waltham, MA, USA) and compared with the fluorescence signal from a control reaction in which the cytotoxic compound was absent and a reaction in which the fluorescence signal was determined for totally lysed cells (where aptamers were replaced by A100 reagent purchased from Chemometec, Allerod, Denmark). On the basis of these readings, the specific cytotoxicity was calculated according to the following formula: [fluorescence (sample)−fluorescence (control)]/[fluorescence (total lysis)−fluorescence (control)]×100.

Figure 12:
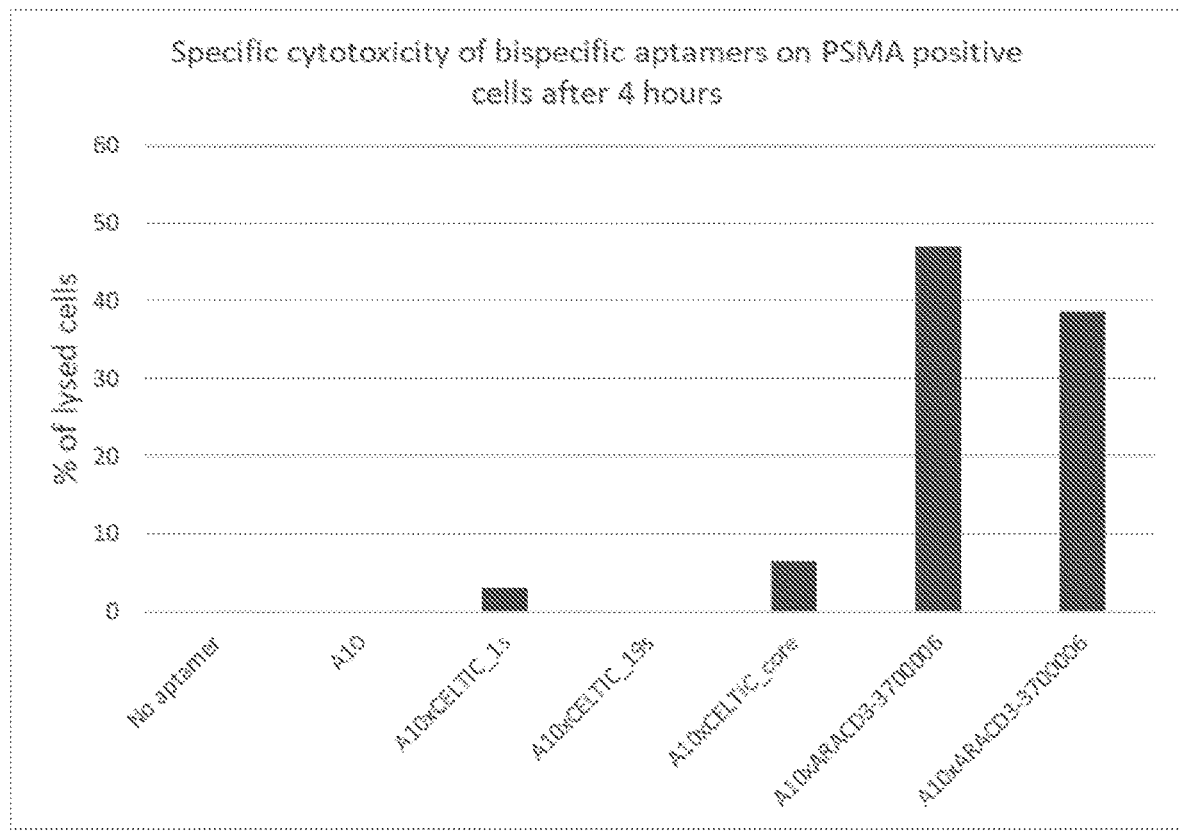
FIG. 12 shows the cytotoxicity of bispecific aptamers towards PSMA-positive cells.

The results of the cytotoxicity assay obtained after 4 h incubation in presence of aptamers 100 nM with a single E:T ratio of 10:1 are shown in FIG. 12. Null to weak specific cell killing activity (<10%) was observed with PSMAxCD3 bispecific RNA/DNA aptamers. Superior specific cytotoxicity was measured with RNA/RNA aptamers A10× ARACD3-3700006 and A10×ARACD3-0010209 that induced the killing of 40-50% of LNCaP cells. Control monomer A10 lacking the CD3 binding moiety did not induce any cytotoxicity.

These results suggest that engineered aptamer switches are able to recruit effector T lymphocytes to target cells to redirect their cytolytic machinery and eliminate a particular cell population.

Example 6. Anti-CAR PNE Aptamers

Library and Primers

The initial RNA library template and primers were synthesized by IDT (Coralville, IA, USA) as single-stranded DNA: 5'-CCTCTCTATGGGCAGTCGGTGAT-(N20)-TTT-CTGCAGCGATTCTTGTTT-(N10)-GGAGAATGAGGA-ACCCAGTGCAG-3' (template, SEQ ID NO:14), 5'-TA-ATACGACTCACTATAGGGCCTCTCTATGGGCAG-TCGGTGAT-3' (forward primer, SEQ ID NO:15), 5'-C-TGCACTGGGTTCCTCATTCTCC-3' (reverse primer, SEQ ID NO:16). Two short "blocking" sequences (purchased from IDT) complementary to the 5'- and 3'-constant primer regions were synthetized to minimize the effect of primers on secondary structure: 5'-ATCACCGACTGCC-CATAGAGAGG-3' (forward blocking sequence, SEQ ID NO:17), 5'-CTGCACTGGGTTCCTCATTCTCC-3' (reverse blocking sequence, SEQ ID NO:18). An additional biotinylated "capture" sequence, complementary to the constant center region of the library was also synthesized by IDT: 5'-Biotin-GTC-PEG-6 Spacer-CAAGAATCG-CTGCAG-3' (SEQ ID NO: 19). All materials were ordered at a 250 nmole scale and underwent desalting purification.

The RNA library for RNA aptamer selection was modified with 2'Fluoro-(2'F-) pyrimidines for greater stability in the final application. T7 primer was combined with library template sequences for primer extension with Titanium Taq DNA polymerase (Clontech; Mountain View, CA, USA). Primer-extended material was then transcribed using the Durascribe® T7 Transcription Kit (Epicentre; Madison, WI, USA), purified on denaturing polyacrylamide with 8 M urea (Sequel NE Reagent, Part A and Part B), which was purchased from American Bioanalytical (Natick, MA, USA). During selection, the library was reverse transcribed using SuperScript IV Reverse Transcriptase (Invitrogen; Carlsbad, CA, USA) according to manufacturer's protocol and amplified using Titanium Taq DNA polymerase from Clontech. During selection, the library was amplified using a following PCR protocol (10 seconds at 95° C., 30 seconds at 60° C., with initial HotStart activation of 60 seconds at 95° C.). RNA library was then transcribed using the Durascribe® T7 Transcription Kit and purified on polyacrylamide gel (PAGE). Gel elution buffer for 4° C. overnight post-purification library recovery was prepared to 0.5 M NH4OAc, 1 mM EDTA (both purchased from Teknova), 0.2% SDS (purchased from Amresco), pH 7.4.

RNA Aptamer Selection

RNA library screening was conducted with six rounds of the selection using a Melting-Off approach. Rounds 1-6 of the selection were performed on a stable HEK293T cell line (Human Embryonic Kidney-ATCC CRL-1573) expressing the GCN4 (S25R14) CAR (Chimeric Antigen Receptor) directed against a peptide neo-epitopes (PNE) on the cell surface and with stably transduced HEK293T cells harboring an anti-CD19 CAR for the negative selection step (cell-SELEX). HEK293T cell line was obtained from American Type Cell Collection and cultured in DMEM medium (Gibco Invitrogen), supplemented with 10% FBS (Gibco Invitrogen) and 1% Penicillin/Steptomycin (Gibco Invitrogen). All selections were performed in DMEM medium supplemented with 10% serum matrix and each of the SELEX rounds included the following steps: immobilization of the RNA library on the streptavidin-coated magnetic beads, counter selection, incubation with the target, reverse transcription of sequences that recognized the target, PCR amplification, and transcription to RNA. Prior to each round, an aliquot of streptavidin-coated magnetic beads (MyOne Streptavidin T1 Dynabeads™, typically 1 pmole of biotinylated material is used with every 20 µg of Dynabead™, amount varied depending on the required stringency) was pre-washed three times with 200 µL PBS-T (final concentration of 0.01% Tween 20, pH 7.4) wash buffer. In addition, target and counter-target cells were harvested with trypsine treatment, pelleted by centrifugation at 5,000×g, and washed twice with DPBS buffer before being suspended in 200 µL of DPBS buffer; number of cells used per round are outlined in Table 1. RNA library was refolded in DMEM medium without serum (1-minute denaturing at 90° C., 5-minute annealing at 60° C., then 5 minutes at 23° C.) with twice the library molar amount of both primer-blocking sequences and the capture sequence. This was done to minimize the effects of the constant primer regions on the secondary structure of aptamers, to allow the library to be captured by the magnetic beads through a streptavidin-biotin binding interaction and to protect the ends of the aptamers from exonucleases.

After refolding and primer blocking, the library was captured on magnetic beads by incubation for 15 minutes at room temperature at room temperature. Magnetic beads were then separated from solution and washed three times with 200 µL of the selection buffer at 37° C. to eliminate any remaining PBS-T and non-specifically bound library species. Magnetic beads with immobilized RNA library underwent then a counter selection incubation in 200 µL of $10_6$ counter-cell preparation at 37° C. for 30 minutes which resulted in releasing the non-specific sequences from the magnetic beads. Non-specific library members were then discarded and the magnetic beads were washed six times for 7 min with 200 µL of the selection buffer over the course of an hour (7 minutes in DPBS at 37° C., 3 minutes to magnetically separate, supernatant was discarded, and the process repeated) to reduce the probability that a non-specific library member may survive to respond during the positive selection step. Positive selection consisted of the incubation of the magnetic beads RNA library with 200 µL of the positive cell preparation at 37° C. for 60 minutes during rounds 1-4 and 30 minutes during rounds 5-6 and the parallel assessments (cell counts in Table 1). Once the positive selection was completed, the supernatant containing the sequences that recognized the target was separated from magnetic beads and recovered. The supernatant then underwent a second magnetic separation in order to ensure that the magnetic beads had been completely removed. Targeted HEK293T CAR PNE cells were pelleted by centrifugation at 5,000×g and washed once with 200 µL of DPBS buffer to remove weakly associated aptamer species. Library was recovered from the cells by heat denaturation at 70° C. Recovered library in all rounds underwent protein precipitation with MPC reagent (Lucigen Corp, Middleton, WI, USA), ethanol precipitation, and concentration of the sample, and were purified by 10% denaturing PAGE with 8 M urea. The library was then reverse-transcribed using SuperScript IV Reverse Transcriptase according to the manufacturer's instructions, amplified using Titanium® Taq DNA polymerase, and transcribed using the Durascribe® T7 Transcription Kit according to the manufacturer's instructions. Transcription products were then purified by 10% denaturing polyacrylamide gel electrophoresis (PAGE) with 8 M urea. Gel slices were excised, eluted overnight at 4° C. in gel elution buffer, and the concentration of RNA library was calculated by measuring the absorbance at 260 nm on NanoDrop-1000. During successive rounds of the SELEX process, the concentration of the RNA library and target cell numbers were gradually decreased. Additional parallel assessments and "cross over fitness test" were performed to facilitate identification of good aptamer candidates during post-selection bioinformatic analysis.

TABLE 1

SELEX conditions used for each selection round of anti-CAR PNE RNA aptamers

| | Counter Selection | | Washes | Positive Selection | | Input |
|---|---|---|---|---|---|---|
| Round | [CAR CD19] | Incubation time | 7 min/ 3 min | [CAR PNE] | Incubation time | Library Picomoles |
| 1 | $1 \times 10^6$ | 30 minutes | 6 | $1 \times 10^6$ | 60 minutes | 1000 |
| 2 | $1 \times 10^6$ | 30 minutes | 6 | $1 \times 10^6$ | 60 minutes | 100 |
| 3 | $1 \times 10^6$ | 30 minutes | 6 | $1 \times 10^6$ | 60 minutes | 100 |
| 4 | $1 \times 10^6$ | 30 minutes | 6 | $1 \times 10^6$ | 60 minutes | 100 |
| 5 | $1 \times 10^6$ | 60 minutes | 6 | $1 \times 10^5$ | 30 minutes | 50 |
| 6 | $1 \times 10^6$ | 60 minutes | 6 | $1 \times 10^5$ | 30 minutes | 100 |
| Parallel (x) | $1 \times 10^6$ | 60 minutes | 6 | $1 \times 10^6$ | 30 minutes | 100 |
| Parallel (+) | $1 \times 10^6$ | 60 minutes | 6 | $1 \times 10^5$ | 30 minutes | 100 |

Aptamer candidates were chosen by next generation sequencing using MiniSeq Mid Output (150 cycle) system (Illumina). Several aptamers were selected for further testing. For this purpose, 2'-Deoxy-2'-fluoro-thymidine-modified RNA aptamers were purchased from Eurogentec-Kaneka (Liège, Belgium) as HPLC-RP purified single stranded oligos synthtized via standard solid phase phosphoramidite chemistry. Biotin was added to the 5'-end of aptamers as a Biotin-TEG that introduces a 16-atom mixed polarity spacer between the aptamer sequence and the biotin flag. Molecular weight, purity and integrity were verified by HPLC-MS. The nucleic acid sequences of these aptamers are shown in FIG. 13A.

Example 7. Determination of the Affinity and Specificity of Anti-CAR PNE Aptamers to Target Expressed on Human Cells The affinity and specificity ARAA-00100001, ARAA-05200001, ARAA-0060095, ARAA-01300011 and ARAA-01700001 aptamers to target proteins expressed on cells were evaluated by flow cytometry. These studies were performed on HEK293T, HEK293T-CAR CD19 (HEK293T cell line transduced with a lentiviral vector encoding for a CAR directed against CD19 antigen) and HEK293T-CAR PNE (HEK293T cell line transduced with a lentiviral vector encoding for a CAR directed against PNE peptide) cells by incubation with biotinylated aptamers in DPBS buffer, supplemented with 5% of FBS. Cells were cultured in DMEM medium (Gibco Invitrogen), supplemented with 10% FBS (Gibco Invitrogen) and 1% Penicillin/Steptomycin (Gibco Invitrogen) prior to use. Prior to experiment, cells ($2.5 \times 10^5$ cells/well) were seeded in 96-well plates and centrifuged at 2500 rpm for 2 min. The supernatant was discarded, and the pelleted cells were washed twice with 200 µL of DPBS-5% FBS buffer preheated at 37° C. Each washing step was followed by centrifugation at 2500 rpm for 2 min. Aptamers were denatured at 85° C. for 5 min and immediately placed on ice block of 4° C. for 5 min. Sequences were subsequently diluted at two different concentration ranges: 30,100 and 300 nM (primary test of 5 aptamer candidates) and 30, 50, 75 and 100 nM (repetition of stainings with ARAA-00100001 and ARAA-01700001) followed by addition of 100 nM phycoerythrin-labelled streptavidin (streptavidin-PE, eBioscience) to each solution. Cells were resuspended in the aptamer dilutions (100 µL/well) and incubated at 37° C. for 30 min in a 5% $CO_2$ humidified atmosphere. As controls, cells were incubated with PNE peptide (Alexa Fluor 488-labelled, Provepharm, Marseille, France), streptavidin-PE (eBioscience) or the respective buffers without additional reagents. After incubation, cells were centrifuged at 2500 rpm for 2 min and the supernatant with unbound sequences was discarded. The pelleted cells were washed with DPBS-5% FBS buffer (200 µL/well) and centrifuged twice in order to remove all weakly and non-specifically attached sequences. The cells were then washed with 1 mg/mL salmon sperm DNA solution (100 µL/well) at 37° C. in a 5% $CO_2$ humidified atmosphere. After 30 min, the salmon sperm solution was removed by centrifugation at 2500 rpm for 2 min and the cells were additionally washed twice with DPBS-5% buffer buffer (200 µL/well) followed by centrifugation. Cells with attached DNA sequences were then fixed (BD CellFIX solution #340181) and the fluorescence-positive cells were counted by flow cytometry (AttuneNXT; Invitrogen, Inc.) on the YL-1 channel.

The results of the binding studies to HEK293T, HEK293T-CAR CD19 and HEK293T-CAR PNE are shown in FIG. 14A. A dose-dependent binding to CAR PNE-positive HEK293T cells was observed with aptamers ARAA-00100001 and ARAA-01700001 without reaching saturation of the signal at the highest tested concentrations. Intensity of the signal was stronger than the PNE peptide control. Residual binding of both aptamers to CAR PNE-negative cells was observed at concentrations above 50 nM. ARAA-05200001, ARAA-0060095 and ARAA-01300011 did not exhibit any differential staining between the three HEK293T cell lines indicating that these three aptamers were not specific for the CAR PNE. Binding studies with aptamers ARAA-00100001 and ARAA-01700001 were repeated over a broader range of concentrations which confirmed results of the primary experiment (see FIGS. 14B and 14C).

Figure 16:
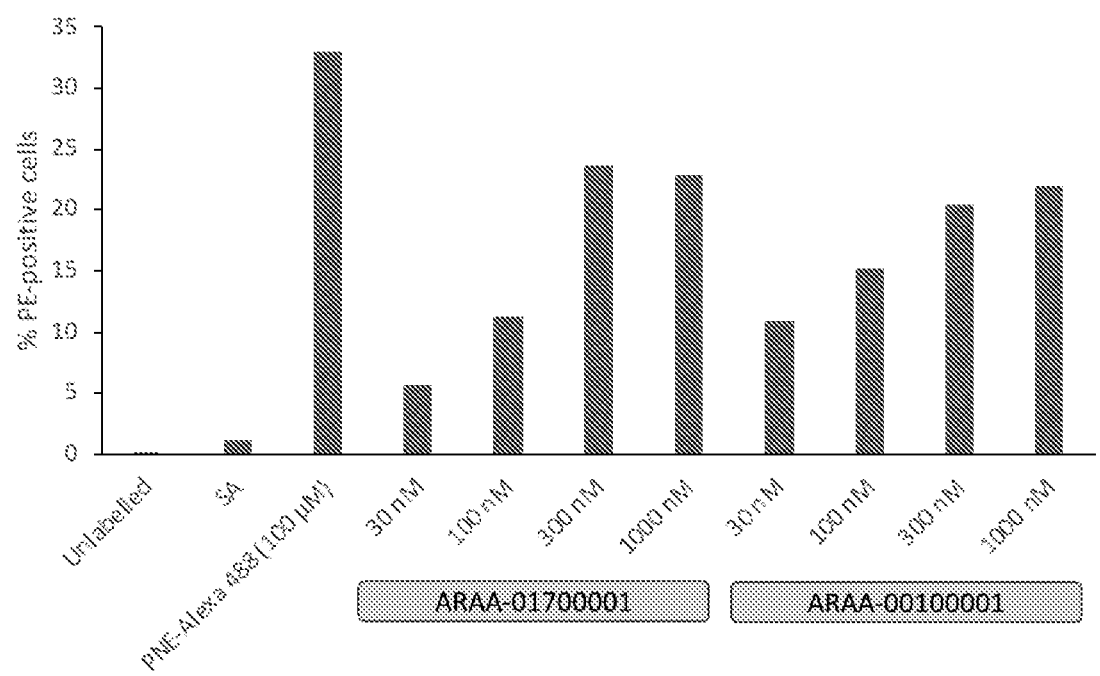
FIG. 16 shows the binding of anti-CAR PNE aptamers to peripheral blood mononuclear cells (PBMC) transduced with a CAR-PNE.

In another experiment, binding of the same aptamers to human PBMCs expressing CAR PNE was investigated. PBMCs were isolated from blood donor as already described in Example 5 and cultured in RPMI-1640 medium (Gibco Invitrogen), supplemented with 10% FBS (Gibco Invitrogen) and 1% Penicillin/Steptomycin (Gibco Invitrogen) at 37° C., 5% $CO_2$. After 2 h transduction with a lentiviral vector encoding for the CAR directed against PNE peptide, cells were kept in culture for additional 72 h before binding studies were performed following the above-described method. As shown in FIG. 16, a dose-dependent signal was measured with both aptamers that reached a plateau at concentrations above 300 nM. Intensity of the signal was stronger than the PNE peptide control.

Both sets of experiments show that ARAA-00100001 and ARAA-01700001 aptamers selected against a CAR that recognizes the PNE peptide are able to specifically recognize their target expressed on human cells that have been engineered to express this particular Chimeric Antigen Receptor.

Example 8. Serum Stability of Aptamers Specific for CAR-PNE

Figure 15:
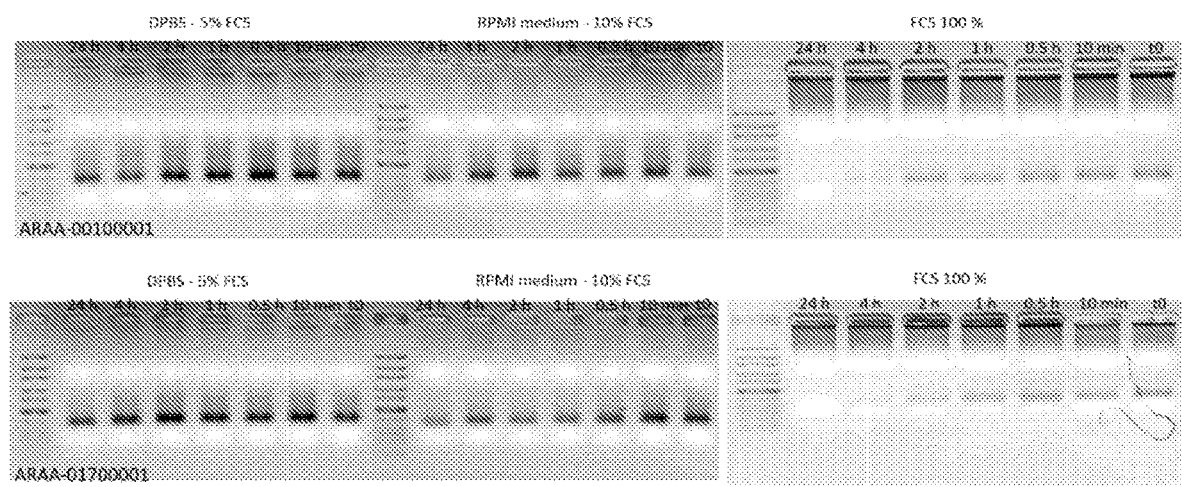
FIG. 15 shows the stability of anti-CAR PNE RNA aptamers in serum.

Stability of anti-CAR PNE RNA aptamers (ARAA-00100001 and ARAA-01700001) was studied in DPBS buffer containing 5% fetal bovine serum (FBS), RPMI medium containing 10% FBS or pure FBS. Aptamers were denatured at 85° C. for 5 min and then immediately cooled on ice block to 4° C. for 5 min. The sequences were then diluted to a final concentration of 2 µM in DPBS buffer supplemented with 5% of FBS, RPMI medium supplemented with 10% FBS or in pure FBS serum. Samples were incubated at 37° C. for 10 min, 30 min, 1 h, 2 h, 4 h or 24 h; the control samples contained the freshly prepared aptamers without incubation at 37° C. Half-life of aptamers in their respective buffers was then determined by migration on agarose gel using denaturing electrophoresis method as follows: aptamer sample from different incubation times were mixed with formamide-containing loading buffer (ThermoScientific, Waltham, MA, USA) and after denaturation at 85° C. for 5 min, 15 µL of each sample was placed on freshly prepared 3% agarose gel containing SYBRsafe (Invitrogen) as a RNA stain marker. The migration of RNA aptamers on agarose gel was performed in 1×TBE buffer (Invitrogen) by applying 100 V during 20 min. The gels were visualized using Bio-Rad imaging system and the results are shown in FIG. 15. Both aptamers were stable for at least 2 h in the different conditions of incubation as the intensity of RNA signals started to decrease after 4 h.

Example 9. Preparation of Bispecific Aptamers Specific for PSMA and CAR-PNE

ARAA-00100001 and ARAA-01700001 aptamers were purchased from baseclick (Neuried, Germany) as HPLC-RP purified 2'-F RNA oligos synthetized via standard solid phase phosphoramidite chemistry.

A10 2'F-RNA aptamer was modified with an azide group at its 3'-end for subsequent triazole inter-nucleotide dimerization. Biotin was added to the 5'-end of A10 aptamer as a Biotin-TEG that introduces a 16-atom mixed polarity spacer between the aptamer sequence and the biotin flag. ARAA-00100001 and ARAA-01700001 were modified with an alkyne group at their 5'-end for subsequent triazole inter-nucleotide dimerization. Molecular weight, purity and integrity were verified by HPLC-MS.

The procedure described in Example 1 was used to prepare bispecific anti-PSMA A10 and anti-CAR PNE aptamers. Results of click reaction are shown in FIG. 8A.

Example 10. Determination of the Affinity and Specificity of Anti-PSMA×Anti-CAR PNE Bispecific Aptamer to Targets Expressed on Cells The affinity and specificity of anti-PSMA×anti-CAR PNE aptamers to target proteins expressed on cells were evaluated by flow cytometry. These studies were performed on PSMA-positive LNCaP (Human Prostate Carcinoma-ATCC CRL-1740) and PSMA-negative PC-3 (Human Prostate Carcinoma-ATCC CRL-1435) in DPBS buffer containing 5% FBS, as described in Example 3. Aptamers were tested within a single concentration range: 30, 100 and 300 nM.

The results of the binding studies to PSMA-positive cells are shown in FIG. 10A. Two RNA/RNA aptamers, A10× ARAA-00100001 and A10×ARAA-01700001 were analyzed along with A10 monomeric aptamer. For comparison, binding of the tested reagents to PSMA-negative PC-3 cells was also measured.

A dose-dependent binding to PSMA-positive LNCaP cells was observed with A10 without reaching saturation of the signal at the highest tested concentrations. Intensity of the signal was as strong as for the antibody control. Residual binding of A10 monomer to PC-3 cells was only observed at the highest tested concentration. Both bispecific PSMA× CAR PNE aptamers exhibited similar binding properties to A10 monomer but with an improved specificity for target-positive cells as residual binding to PSMA-negative cells was reduced. For each tested concentration, signal intensity of bispecific aptamers was superior to the one measured for A10 monomer, suggesting that heterodimerization resulted in an improvement of the affinity.

Altogether the results from Examples 9 and 10 suggest that the heterodimerization of aptamers selected against different targets does not significantly impact the binding properties of each moiety when evaluated separately.

Example 11. Bioactivity of Bispecific Aptamers Specific for CAR-PNE and PSMA

Cytotoxicity assays are carried out on unstimulated peripheral blood mononuclear cells (PBMCs). Freshly prepared PBMCs are isolated from buffy coats obtained from healthy donors (Etablissement Français du Sang, Division Rhônes-Alpes). After diluting the blood with DPBS, the PBMCs are separated over a FICOLL density gradient (FICOLL-PAQUE PREMIUM 1.077 GE Healthcare), washed twice with DPBS, resuspended in RPMI-1640 medium (Gibco Invitrogen) to obtain a cell density of $5\times10_6$ cells/ml. These PBMCs are transduced with lentiviral vectors expressing the CAR-PNE receptor. These PBMC-CAR-PNE are used as effector cells.

LNCaP target cells are labeled with 2 µM calcein AM (Trevigen Inc, Gaithersburg, MD, USA) for 30 min at 37° C. in cell culture medium. The calcein AM fluorochrome is a dye that is trapped inside live LNCaP cells and only released upon redirected lysis. After 2 washes in cell culture medium, a cell density of $5\times10^5$ cells/ml is adjusted in RPMI-1640 medium and 100 µl aliquots of 50,000 cells are used per assay reaction. A standard reaction at 37° C./5% $CO_2$ lasts for 4 hr and uses $5\times10^4$ cells calcein AM-labeled target cells, $5\times10^5$ PBMCs-CAR-PNE (E/T ratio of 1:10) and 20 µl of bispecific aptamer solutions at 1 µM in a total volume of 200 µl. After the cytotoxic reaction, the released dye in the incubation medium is quantitated in a fluorescence reader (VarioSkan Lux, ThermoFisher, Waltham, MA, USA) and compared with the fluorescence signal from a control reaction in which the cytotoxic compound is absent and a reaction in which the fluorescence signal was determined for totally lysed cells (where aptamers were replaced by A100 reagent purchased from Chemometec, Allerod, Denmark). On the basis of these readings, the specific cytotoxicity is calculated according to the following formula: [fluorescence (sample)−fluorescence (control)]/[fluorescence (total lysis)−fluorescence (control)]×100.

The results of the cytotoxicity assay obtained after 4 h incubation in presence of aptamers 100 nM with a single E:T ratio of 10:1 are determined. Specific cytotoxicity is measured with RNA/RNA aptamers A10×PNE that induce the killing of more than 30% of LNCaP cells. Control monomer A10 lacking the PNE binding moiety does not induce any cytotoxicity.

The results can be used to show that engineered aptamer switches are able to recruit effector T lymphocytes to target cells to redirect their cytolytic machinery and eliminate a particular cell population.

Example 12. Treatment of Cancer in a Preclinical Model with Anti-CD3×Anti-PSMA Aptamer In vivo efficacy and toxicity of different multimeric aptamer constructs in comparison to monomeric aptamers in mice are evaluated. Adult mice bearing PSMA positive tumors are administered with aptamers that specifically bind to CD3 and PSMA, in different groups of mice, the aptamers are either in monomeric form or multimeric form. Efficacy is evaluated by measuring tumor size, tumor growth and rate, and survival in the treated groups versus controls. Toxicity is assessed by the incidence of adverse reactions in treated groups versus controls.

Example 13. Treatment of Cancer in a Preclinical Model with a CAR-T Aptameric Switch In vivo efficacy and toxicity of switch aptamer constructs in comparison to monomeric aptamers in mice are evaluated. Multimeric aptamers are prepared as switches that will turn on the activity of CAR T-cell based therapeutics. Adult mice bearing tumors are first injected with T cells transduced with CAR PNE and the multimeric aptamer made of an anti-CAR PNE aptamer fused to PSMA, or HER2, or CD19, or CD20 or CD22 tumor associated targets is infused. Efficacy is evaluated by measuring tumor size, tumor growth and rate, and survival in the treated groups versus controls. Toxicity is assessed by the incidence of adverse reactions in treated groups versus controls.

The content of the ASCII text file of the sequence listing named "Substitute-Sequence-Listing-12269-0204_ST25", having a size of 5.14 kb and a creation date of 2 Jan. 2024, and electronically submitted via Patent Center on 2 Jan. 2024, is incorporated herein by reference in its entirety.

As used herein, "consisting essentially of" allows the inclusion of materials or steps that do not materially affect the basic and novel characteristics of the claim. Any recitation herein of the term "comprising", particularly in a description of components of a composition or in a description of elements of a device, can be exchanged with "consisting essentially of" or "consisting of".

While the present technology has been described in conjunction with certain preferred embodiments, one of ordinary skill, after reading the foregoing specification, will be able to effect various changes, substitutions of equivalents, and other alterations to the compositions and methods set forth herein.

REFERENCES

Dassie J P, et al., Systemic administration of optimized aptamer-siRNA chimeras promotes regression of PSMA-expressing tumors. Nat. Biotechnol 27, 839 (2009).
Di Stasi A, et al., Inducible apoptosis as a safety switch for adoptive cell therapy. N Engl J Med 365, 1673 (2011).
McNamara J O, et al., Cell type-specific delivery of siRNAs with aptamer-siRNA chimeras. Nat. Biotechnol 24, 1005 (2006).
Rodgers D T, et al., Switch-mediated activation and retargeting of CAR-T cells for B-cell malignancies, PNAS 113, E459 (2016).
Straathof K C, et al., An inducible caspase 9 safety switch for T-cell therapy. Blood 105, 4247 (2005).
Tamada K, et al., Redirecting gene-modified T cells toward various cancer types using tagged antibodies. Clin Cancer Res 18, 6436 (2012).
Urbanska K, et al., A universal strategy for adoptive immunotherapy of cancer through use of a novel T-cell antigen receptor. Cancer Res 72, 1844 (2012a).
Urbanska K, et al., Development of a novel universal immune receptor for antigen targeting: To infinity and beyond, OncoImmunology 1, 777 (2012b).
Wu C Y, et al., Remote control of therapeutic T cells through a small molecule-gated chimeric receptor, Science 350, aab4077 (2015).

What is claimed is:

1. An aptameric bridge for binding a chimeric antigen receptor (CAR) to a target, wherein an extracellular domain of the CAR is capable of specifically binding a peptide neo-epitope (PNE), the bridge comprising one or more CAR-binding aptamers and one or more target-binding aptamers, wherein the one or more CAR-binding aptamers are connected by one or more linkers to the target-binding aptamers, and wherein at least one of the one or more CAR-binding aptamers binds to the extracellular domain of the CAR.

2. The aptameric bridge of claim 1, wherein binding of a CAR-binding aptamer of the bridge to the CAR expressed on an immune cell activates the immune cell.

3. The aptameric bridge of claim 1, wherein binding of a CAR-binding aptamer of the bridge to the CAR expressed on an immune cell does not activate the immune cell.

4. The aptameric bridge of claim 2, wherein the immune cell is a T-cell, NK-cell, or macrophage, and said binding leads to destruction of a target cell bound to a target-binding aptamer of the aptameric bridge.

5. The aptameric bridge of claim 1, wherein the linker comprises or consists of a linker moiety selected from the group consisting of a covalent bond, a single-stranded nucleic acid, a double-stranded nucleic acid, a peptide, a polypeptide, an oligosaccharide, a polysaccharide, a synthetic polymer, a hydrazone, a thioether, an ester, a triazole, a nanoparticle, a micelle, a liposome, a cell, and combinations thereof.

6. The aptameric bridge of claim 1 that does not contain an immunoglobulin peptide or fragment thereof.

7. The aptameric bridge of claim 1 that does not contain a peptide or polypeptide.

8. The aptameric bridge of claim 5, wherein the linker moiety comprises a single-stranded or double-stranded nucleic acid selected from DNA, RNA, and XNA.

9. The aptameric bridge of claim 5, wherein the linker moiety is an immunoglobulin polypeptide or fragment thereof.

10. The aptameric bridge of claim 5, wherein the linker moiety is a polysaccharide selected from the group consisting of glucan, dextran, glycogen, starch, and derivatives thereof.

11. The aptameric bridge of claim 5, wherein the linker moiety is a synthetic polymer selected from poly(amidoamine) (PAMAM) and poly(beta amino ester) (PBAE).

12. The aptameric bridge of claim 1, wherein the CAR extracellular domain comprises an immunoglobulin polypeptide or fragment or derivative thereof.

13. The aptameric bridge of claim 9, wherein the immunoglobulin polypeptide is a single chain Fv.

14. The aptameric bridge of claim 1, wherein the PNE consists of an amino acid sequence not found in the human proteome.

15. The aptameric bridge of claim 1, wherein the PNE is selected from the group consisting of SEQ ID NOS: 1-7.

16. The aptameric bridge of claim 1, wherein at least one of the target-binding aptamers binds a target selected from the group consisting of CD19, CD20, CD22, CD123, BCMA, NY-ESO-1, mesothelin, PSA, PSMA, MART-1, MART-2, Gp100, tyrosinase, p53, ras, MUC1, SAP-1, survivin, CEA, Ep-CAM, Her2, EGFRVIII, BRCA1/2, CD70, CD73, and mutated SOD.

17. The aptameric bridge of claim 1, comprising two or more identical or non-identical CAR-binding aptamers.

18. The aptameric bridge of claim 17, comprising two or more identical or non-identical target-binding aptamers.

19. The aptameric bridge of claim 1 that comprises a molecular form selected from the group consisting of ring-shaped, star-shaped, dendrimeric, linear, branched, and combinations thereof.

20. The aptameric bridge of claim 1 that has a distance between one or more of the CAR-binding aptamers and one or more of the target-binding aptamers in the range from about 70 to about 200 angstroms.

21. The aptameric bridge of claim 1 that binds to said CAR when expressed in a T cell, NK cell, B cell, or macrophage.

22. The aptameric bridge of claim 21 that activates said T cell, NK cell, B cell, or macrophage upon binding to said CAR.

23. The aptameric bridge of claim 1, wherein the one or more CAR-binding aptamers and the one or more target-binding aptamers each have a binding affinity of less than 10 nM.

24. A system for immunotherapy, the system comprising the aptameric bridge of claim 1 and an immune cell expressing said CAR.

25. A kit for providing immunotherapy to a subject, the kit comprising the aptameric bridge of claim 1 and a viral vector encoding said CAR.

26. A method of performing immunotherapy in a subject in need thereof, the method comprising the steps of:
(a) administering to the subject a population of cells expressing a CAR, wherein the CAR comprises an extracellular domain that is capable of specifically binding a peptide neo-epitope (PNE); and
(b) administering to the subject the aptameric bridge of claim 1;
whereby the aptameric bridge binds to CAR-expressing cells in the subject and induces an interaction between the CAR-expressing cells and the target.

* * * * *